United States Patent
Ito

(10) Patent No.: US 6,628,457 B2
(45) Date of Patent: Sep. 30, 2003

(54) ANTIVIBRATION MICROSCOPE

(75) Inventor: Eiichi Ito, Tokyo (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 207 days.

(21) Appl. No.: 09/900,942

(22) Filed: Jul. 9, 2001

(65) Prior Publication Data

US 2002/0085273 A1 Jul. 4, 2002

(30) Foreign Application Priority Data

Jul. 11, 2000 (JP) ........................ P2000-209791

(51) Int. Cl.[7] .............................................. G02B 21/00

(52) U.S. Cl. .................. 359/368; 359/369; 359/554

(58) Field of Search .................. 359/368, 369, 359/384, 554–557; 248/280.11, 281.11

(56) References Cited

U.S. PATENT DOCUMENTS 5,786,936 A * 7/1998 Baumann et al. .......... 359/557

* cited by examiner

*Primary Examiner*—Mark A. Robinson
*Assistant Examiner*—Lee Fineman
(74) *Attorney, Agent, or Firm*—Pitney, Hardin, Kipp & Szuch LLP

(57) ABSTRACT

Angular speed sensors and acceleration sensors are built into the casing of a video-type stereoscopic microscope. The angle of rotation of the stereoscopic microscope detected by the angular speed sensors and the amount of shift of the stereoscopic microscope detected by the acceleration sensors are input to a microscope control unit. This microscope control unit controls a vibration compensator based on the result of the detection. The vibration compensator shifts a lens within a plane orthogonal to its the optical axis so that object light from a field is deflected to a direction parallel to the optical axes of individual zoom optical systems. The vertical width $A_V$ of the field and the working distance L of this video microscope satisfy the following inequality:

$$1/A_V > 1/(11.46 + 0.011 \times L).$$

6 Claims, 42 Drawing Sheets

ANTIVIBRATION MICROSCOPE

BACKGROUND OF THE INVENTION

1. Field of the Invention

The invention relates to a microscope to be supported at an extremity of a pedestal for use.

2. Description of the Related Art

An optical-type or video-type microscope is used at an occasion of fine tissue treatment such as a neurosurgical operation, because the tissue is difficult to distinguish under naked eyes. Here, the observer using this microscope is a doctor who is performing the operation (hereinafter, referred to as "chief operator"). Since both hands of the chief operator are occupied by knifes or the like, this microscope must be held by a pedestal. Moreover, due to a necessity to shoot various locations of the patient from various directions, this pedestal must be provided with a long arm which supports the microscope at its extremity and is freely bendable to various directions. When the microscope is supported at the extremity of such an arm, the microscope inevitably makes tremors. Nevertheless, conventional microscopes have a working distance (i.e., the distance from vertex of the the object side face of a microscope optical system to the object-side focus of the same) of short length, no longer than 300 mm at best. Besides, the range of observation through a microscope optical system within the plane perpendicular to the optical axis of the microscope optical system at its object-side focus (hereinafter, referred to as "field") is not so small, having a vertical dimension of the order of 15 mm. In other words, the microscope optical systems are not so high in overall magnification. Therefore, even if the microscopes are held at the arm extremities and therefore the microscopes make tremors, these tremors have little effect on the image under observation. Accordingly, there has been no problem in practice.

When a microscope is used in surgical operations, however, it is desired that the microscope have a working distance of not shorter than 300 mm so as to prevent the microscope itself from interfering with the operations. Once the working distance is extended thus, tremors of the microscope shifts the field with respect to the object of observation to such an extent as recognizable with the resolution of the observer's eye. Besides, an increase in magnification is also desired of microscopes. However, increased magnifications of the microscopes narrow the field, increasing the ratio of range of shifting to the size of the field. In other words, expansion rare of the range of shifting to the size of the field through the microscope optical systems increases. As a result, the observer recognizes that image of the object blurs, with a significant deterioration in the apparent optical performance.

SUMMARY OF THE INVENTION

The present invention has been achived in recognition of the foregoing problems. It is an object of the present invention to incorporate a mechanism for preventing blur of image into a microscope that has a high probability of causing image blur as great as recognizable by observer's eyes when held at the extremity of an arm of a pedestal.

According to a first aspect of the present invention, an antivibration microscope includes a microscope optical system which forms an image of an object lying in a field of a predetermined size and whose working distance L satisfies the condition: $1/A_V > 1/(11.46 + 0.011 \times L)$, where $A_V$ is the width of the field to be observed; a first sensor for measuring inclination of the whole microscope optical system; a second sensor for measuring movement of the whole microscope optical system; a deflecting device which deflects object light traveling through the microscope optical system to an arbitrary direction at an arbitrary angle; and a controlling unit for adjusting the direction and angle of deflection for the object light by the deflecting device based on the measurements by the first sensor and the second sensor, whereby said image is steady in spite of the inclination or the movement of the microscope optical system.

With the microscope optical system satisfing the above-described condition, the microscope has a high possibility of producing image blur as great as recognizable to the eyes of the observer who observes the image of the field through the microscope optical system in case it is fixed to an extremity of an arm of a pedestal. On that account, this microscope is incorporated with an antivibration mechanism composed of the first sensor, the second sensor, the controlling unit, and the deflecting device. As a result, image blur highly probable to occur in this microscope is surely prevented by the antivibration mechanism, so that the deterioration in the apparent optical performance does not occur.

The microscope optical system may be an optical system of a so-called optical microscope in which the image of the field once formed by an objective optical system is observed by the observer through an eyepiece lens. Alternatively, it may be an optical system of a so-called video-type microscope in which the image of the field formed by an objective optical system is picked up to be displayed on a monitor. Moreover, this microscope optical system may be a monocular optical system, or a binocular optical system.

The first sensor may be an angular speed sensor or an angular acceleration sensor. The fisrt sensor is desirably provided in two to measure the angle in two orthogonal directions, respectively.

The second sensor may be a position sensor or an acceleraton sensor. The second sensor is desirably provided in two to measure the movement in two orthgonal directions, respectively.

The deflecting device may include a mechanism for shifting a lens with a power that is included in the microscope optical system to a direction orthogonal to its optical axis. The deflecting device may also include a mechanism for adjusting the direction of inclination and the angle of inclination of a reflecting mirror inserted into the microscope optical system. Alternatively, the deflecting device may include a variable-angle prism. The deflecting device may effect the deflection for the object light at any position in the microscope optical system.

An antivibration microscope according to a second aspect of the present invetion includes a microscope optical system which forms an image of an object lying in a field of a predetermined size and whose working distance L satisfies the condition: $1/A_V > 1/(11.46 + 0.011 \times L)$, where $A_V$ is the width of the field; an image pickup device having an image taking surface which picks up the image formed on the image taking surface by the microscope optical system; a first sensor for measuring inclination of the whole microscope optical system; a second sensor for measuring movement of the whole microscope optical system; and a controlling unit for moving the image pickup device within a plane including the image taking surface based on the measurements of the first sensor and the second sensor so that the image of the object, lying in a predetermined field, formed by the microscope optical system can be picked up at a fixed position on the image taking surface of the image pickup device.

With the microscope optical system satisfing the above-described condition, the microscope has a high possibility of producing image blur as great as recognizable to the eyes of the observer who observes the image picked up by the image pickup device on a monitor in case it is fixed to an extremity of an arm of a pedestal. On that account, this microscope is incorporated with an antivibration mechanism composed of the first sensor, the second sensor, the controlling unit, and the image pickup device. As a result, image blur highly probable to occur in this microscope is surely prevented by the antivibration mechanism, so that the deterioration in the apparent optical performance does not occur.

BRIEF DESCRIPTION OF DRAWINGS

The invention will be described below in detail with reference to the accompanying drawing, in which.

DESCRIPTION OF THE PREFERRED EMBODIMENT

The preferred embodiments of the present invention will now be described in detail below with reference to the accompanying drawings.

In each of the following embodiments, an antivibration microscope according to the present invention is embodied as an video-type stereoscopic microscope (hereinafter, referred to as "stereoscopic microscope" for simplicity) in which stereovision image of an object is formed on an image taking surface of an image pickup device by a pair of image taking optical system, and an image signal converted from the stereovision image by the image pickup device is output.

The "stereoscopic microscope" is incorporated in a surgical operation supporting system that is used in cerebral surgical operations, for example. In this surgical operation supporting system, the three-dimensional image (stereovision image) of a tissue of a patient, which is photographed by the stereoscopic microscope is displayed on a stereoscopic viewer for a lead surgeon and on monitors for other staffs, and simultaneously recorded by a recording device.

Figure 1:
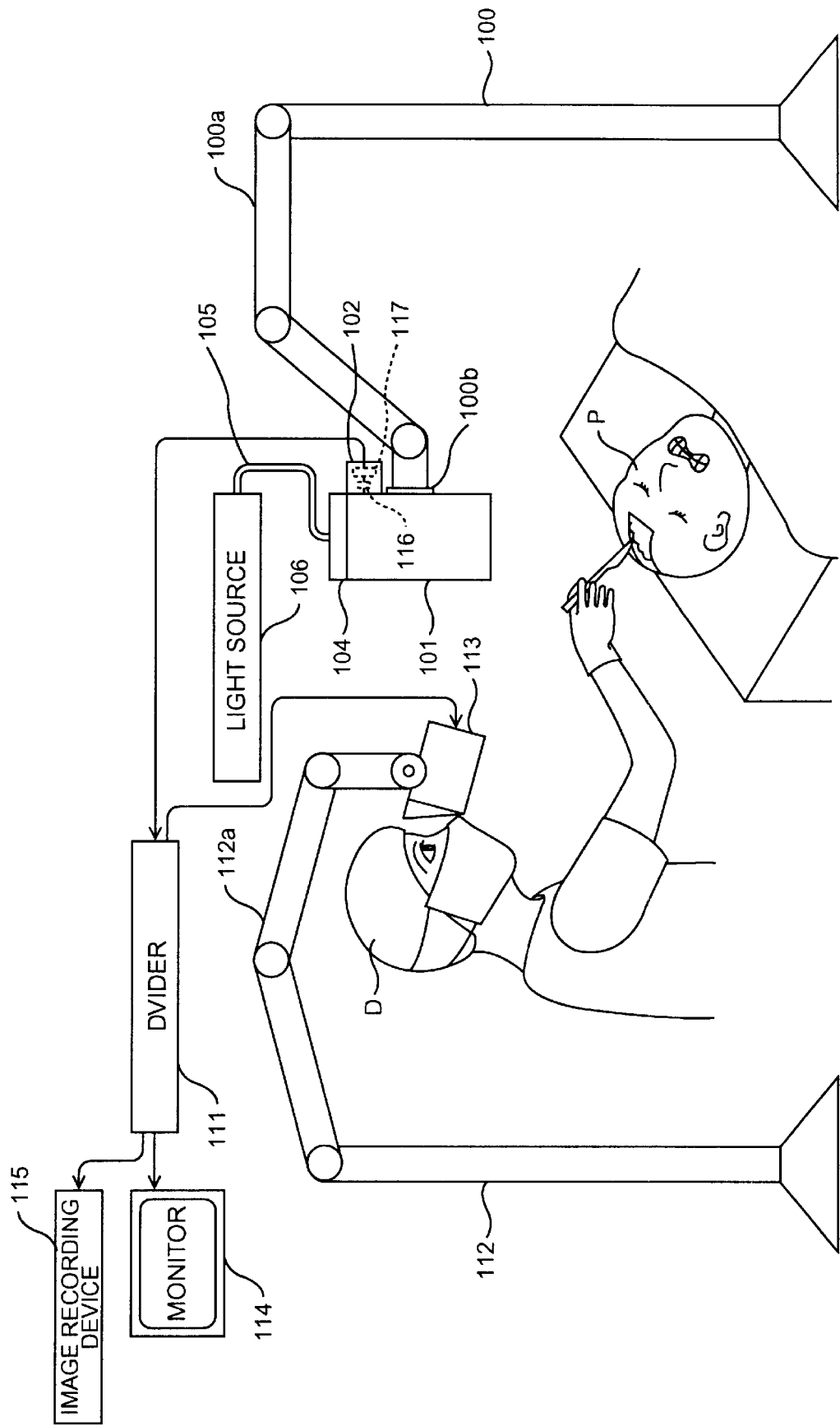
FIG. 1 is a schematic view showing an overall construction of a surgical operation support system equipped with a video-type stereoscopic microscope according to first embodiment of the present invention.

First Embodiment
The Overall Configuration of the Surgical Operation Supporting System FIG. 1 schematically shows an arrangement of the surgical operation supporting system. As shown in this figure, the surgical operation supporting system is composed of a stereoscopic microscope 101, a high definition CCD camera 102 attached on the upper end of the back surface of the stereoscopic microscope 101, a counter weight 104 attached on the top of the stereoscopic microscope 101, a light guide fiber bundle 105 inserted into the interior of the stereoscopic microscope 101 through a center hole formed in the counter weight 104, a light source 106 emitting illumination light to be introduced into the stereoscopic microscope 101 through the light guide fiber bundle 105, a divider 111 connected to the high definition CCD camera 102, an image recording device 115, a monitor 114 and a stereoscopic viewer 113 which are connected to the divider 111.

The stereoscopic microscope 101 has a mount on its back surface and is detachably fixed to the distal end of a free arm 100a of a first stand 100 through the mount. The free arm 100a is assembled from three arms connected in live via two universal joints which allow the arms to be relatively folded in an arbitrary direction and at an arbitrary angle. Total length of the free arm 100a is 1000 mm. Thus, the stereoscopic microscope 101 can be moved within the space where the free arm 100a of the first stand 100 can reach, and can also be inclined in an arbitrary direction. Hereinafter, the object side (that is, patient side) relative to the stereoscopic microscope 101 will be defined as "low", and the opposite side as "high" so that understanding thereof may be easy.

Since the optical configuration in this stereoscopic microscope 101 will be explained in detail later, only its schematics will be explained here.

Figure 2:
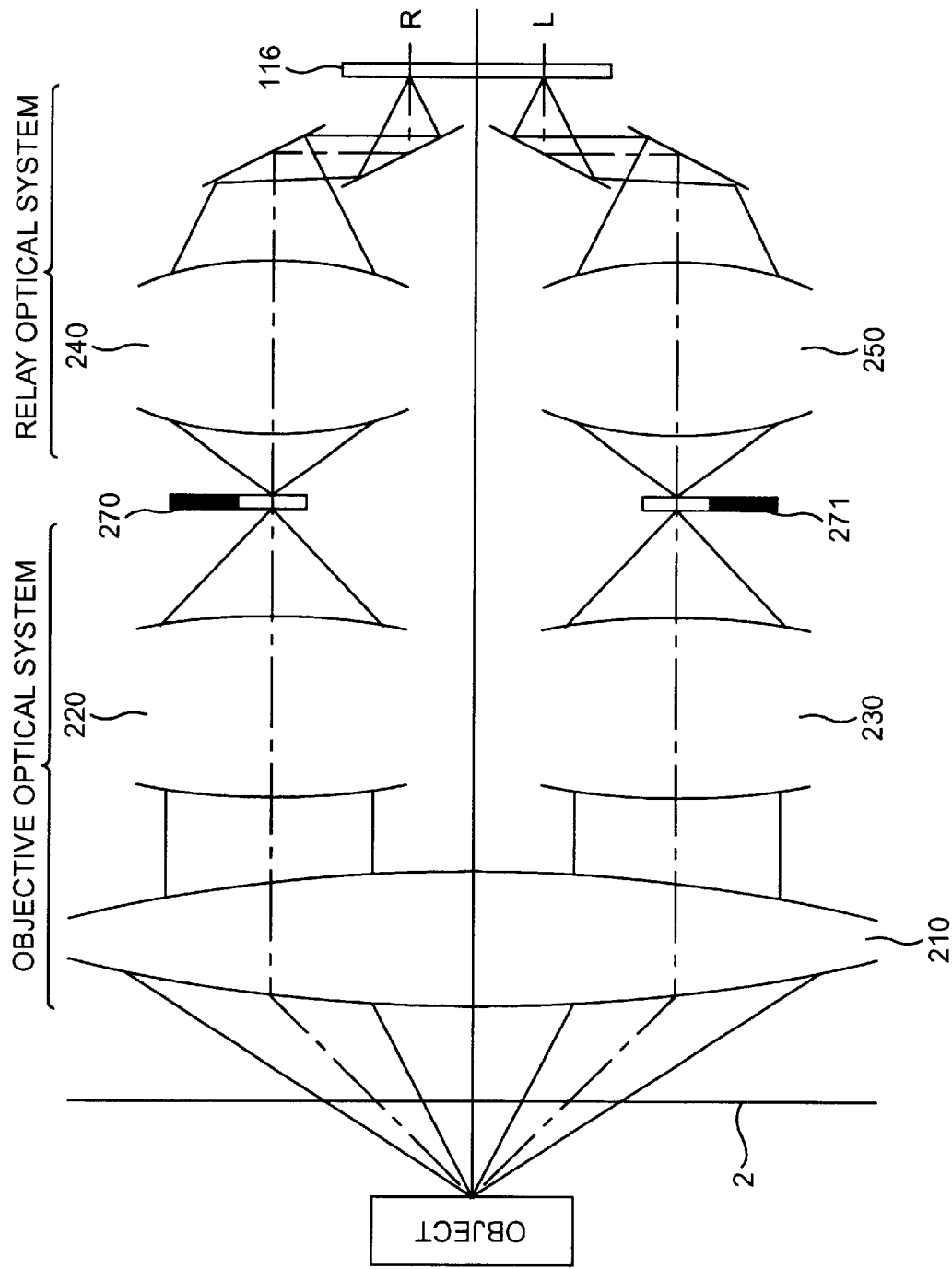
FIG. 2 is a schematic view showing an optical construction in the video-type stereoscopic microscope.

As shown in FIG. 2, primary images of an object are formed as aerial images at respective positions of right and left field stops 270, 271 through an objective optical systems including a large-diameter close-up optical system 210 having a single optical axis and a pair of right and left zoom optical systems 220, 230, which respectively focus light rays that have passed through different portions of the close-up optical system 210. A pair of right and left relay optical systems 240, 250 relay the right and left primary images to form right and left secondary images on the right and left image taking regions in an image taking surface of a CCD 116 mounted in the high definition CCD camera 102, respectively. Each of the image taking regions has a vertical to horizontal aspect ratio of 9:8, while the image taking surface of the CCD 116 has a "high definition" size of which aspect ratio of vertical to horizontal is 9:16.

The images which are thus formed on the right and left image taking regions of the image taking surface of the CCD 116 through the pair of image taking optical systems are equivalent to stereovision images including a pair of images taken from two locations which are separated from each other by the predetermined base length, which are arranged side by side. An output signal from this CCD 116 is converted to a high definition video signal by the image processor 117, and is outputted from the high definition CCD camera 102 to the divider 111.

The stereoscopic microscope 101 contains an illuminating optical system 300 (see FIG. 6) for illuminating the object that is located in the vicinity of the focal point of the close-up optical system 210. Illuminating light from the light source 106 is introduced into this illuminating optical system 300 via the light guide fiber bundle 105.

Returning to FIG. 1, the high definition video signal showing the object, which is outputted from the high definition CCD camera 102, is divided by the divider 111, and is supplied to the stereoscopic viewer 113 for a lead surgeon, to the monitor 114 for other surgical staffs or an advisor at a remote location, and to the recording device 115, respectively.

Figure 3:
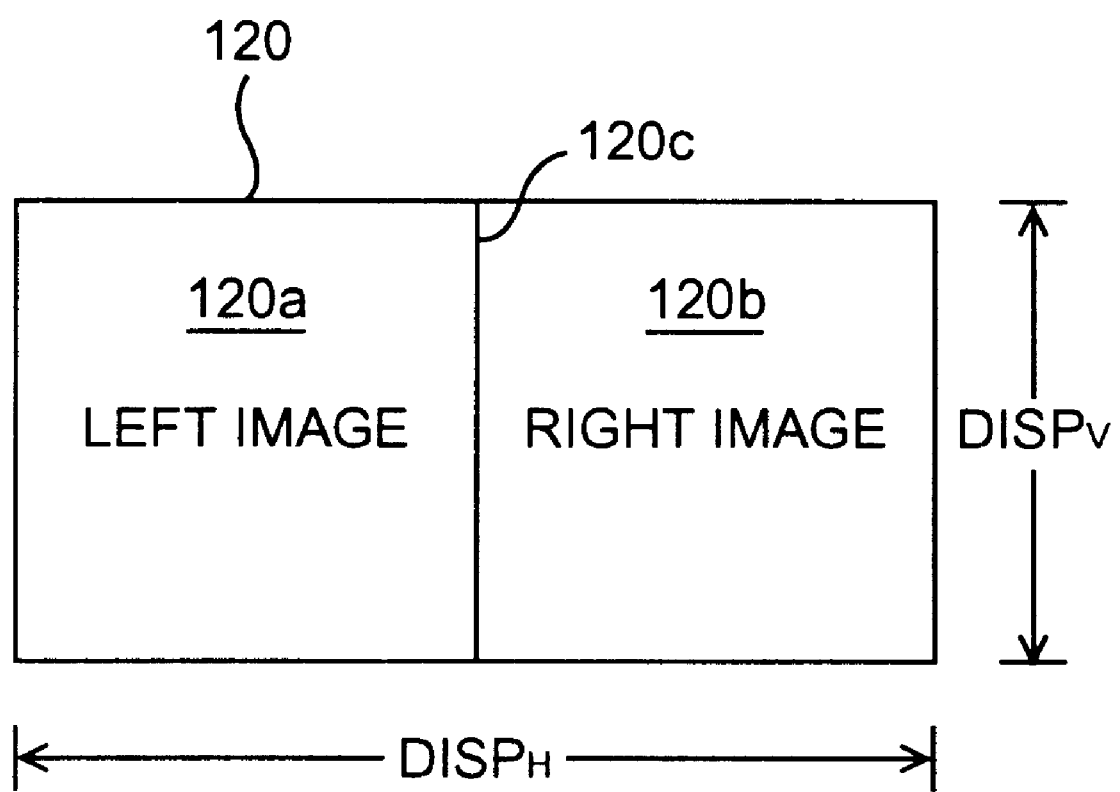
FIG. 3 is a plan view of an LCD panel.
Figure 4A:
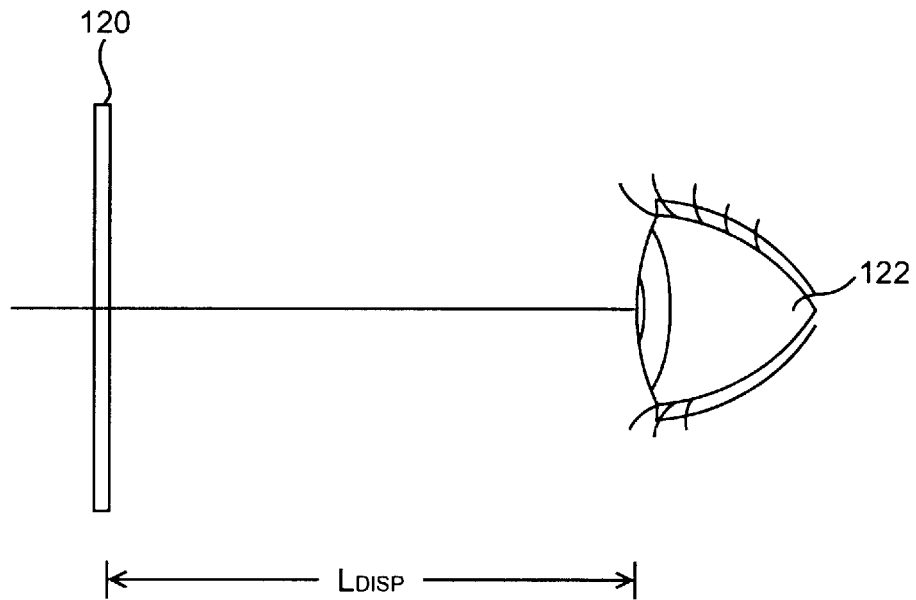
FIGS. 4A and 4B are a schematic view showing an optical construction of a video-type stereoscopic viewer.
Figure 4B:
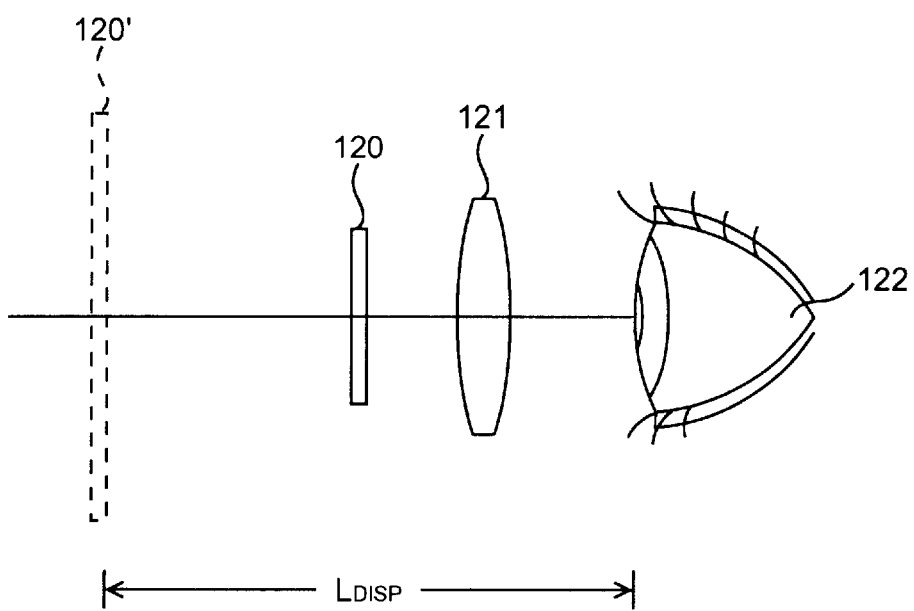

The stereoscopic viewer 113 is attached to the distal end of a free arm 112a of a second stand 112 in the downward direction, so that the stereoscopic viewer 113 can be suitably positioned in accordance with a posture of the lead surgeon that facilitates his/her operations. The stereoscopic viewer 113 contains a high-definition-sized LCD panel 120 having an aspect ratio of 9:16 as a monitor. When the high definition video signal from the divider 111 is inputted into the LCD panel 120, as shown in the plan view of FIG. 3, the left half 120a of the LCD panel 120 displays the image taken by the left image taking region of CCD 116, and the right half 120b thereof displays the image taken by the right image taking region of CCD 116. The light paths in the stereoscopic viewer 113 are divided into the right and the left by a partition 121, which is installed along a direction perpendicular to the LCD panel 120 at the boundary 120c of the left and right halves 120a, 120b of the LCD panel 120. The image on the left half 120b is observed by the left eye of the chief operator which is put on the left side of the diaphragm. The image on the right half 120a is observed by the right eye of the chief operator which is put on the right side of the diaphragm. FIG. 4A shows the relative positions of the LCD panel 120 and the eyes 122 as seen from beside the operator. As shown in this FIG. 4A, the eyes 122 of the chief operator are positioned a predetermined distance LDISP away from the LCD panel 120 with not-shown eye holes so that the eyes 122 can naturally observe the LCD panel 120. FIG. 4B shows a variation of the stereoscopic view 113. As shown in this FIG. 4B, eyepiece lenses 121 for regulating the positions of the eyes 122 and forming virtual images 120' of the LCD panel 120 beyond the LCD 120 may be arranged between the LCD panel 120 and the eyes 122. In this case, the focal lengths of the eyepiece lenses 121 and the position of the LCD panel 120 are determined so that the virtual images 120' of the LCD panel 120 are formed a predetermined distance $L_{DISP}$ away from the eyes 122 which are placed just behind the eyepiece lenses 121. Incidentally, the vertical width and horizontal width of the LCD panel 120 (or the virtual images 120' of the LCD panel 120) of the stereoscopic viewer 113 will hereinafter be indicated as $DISP_V$ and $DISP_H$, respectively.

The Configuration of the Stereoscopic Microscope

Figure 5:
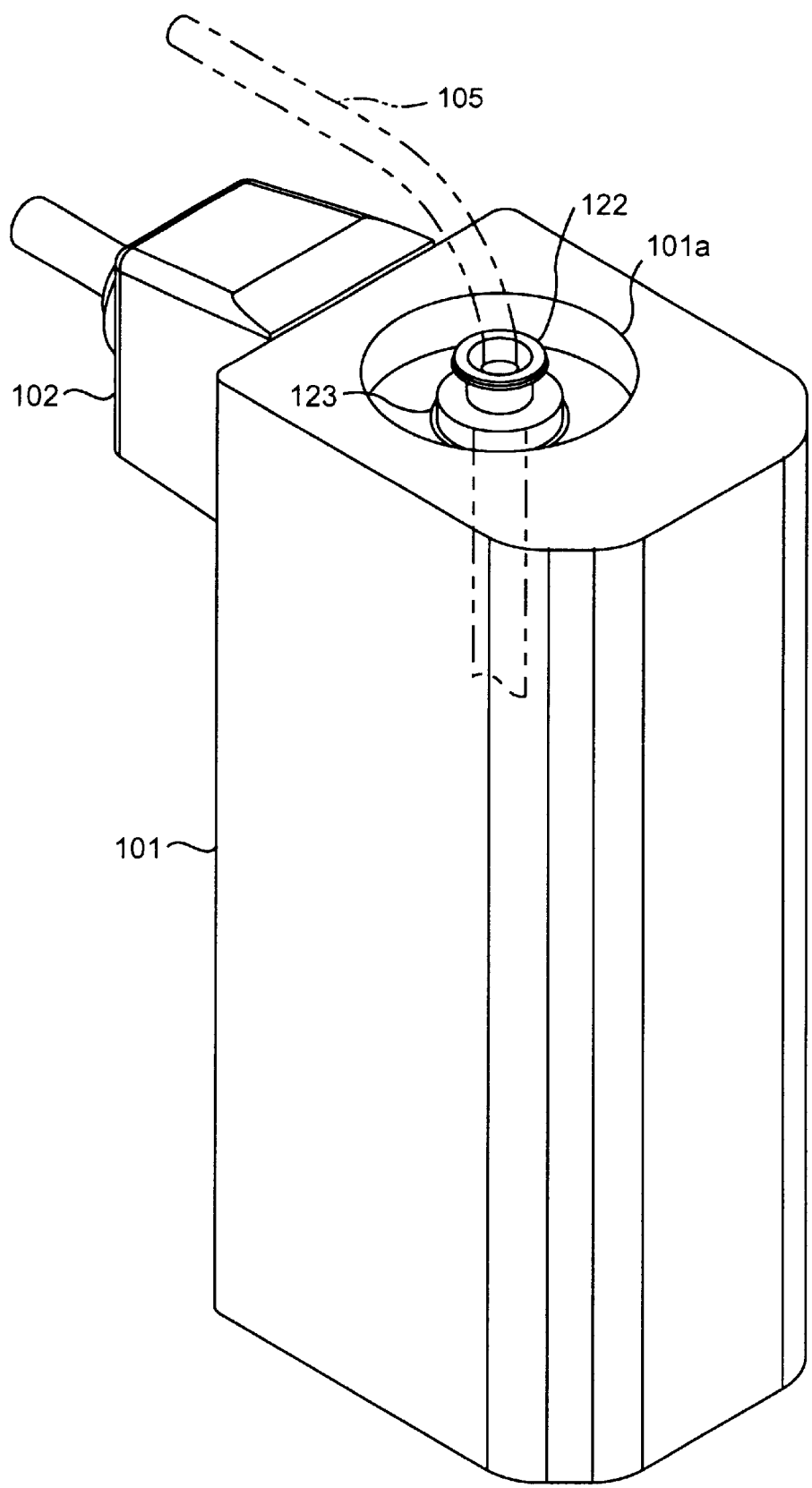
FIG. 5 is a perspective view showing an outer appearance of the stereoscopic microscope.

The structure of the above-mentioned stereoscopic microscope 101 (including the high definition CCD camera 102) is explained in more detail. As shown in FIG. 5, this stereoscopic microscope 101 has a shape of substantially polygonal column. The back surface of the stereoscopic microscope 101 is flat and is attached with the high definition CCD camera 102, and the front surface (that is, the opposite side of the back surface) has chamfered edges on both sides. At the center of the top surface, a circular recess 101a is formed. At the center of the recess 101a, an insertion opening (not illustrated) is bored so as to be inserted with a guide pipe 122, which is a cylindrical member fixedly covering the distal end of the light guide fiber bundle 105. Here, an annular-shaped member (that is, fiber guide insertion part) 123 attached to the insertion opening is a chuck for fixing the guide pipe 122 inserted into the insertion opening.

Figure 6:
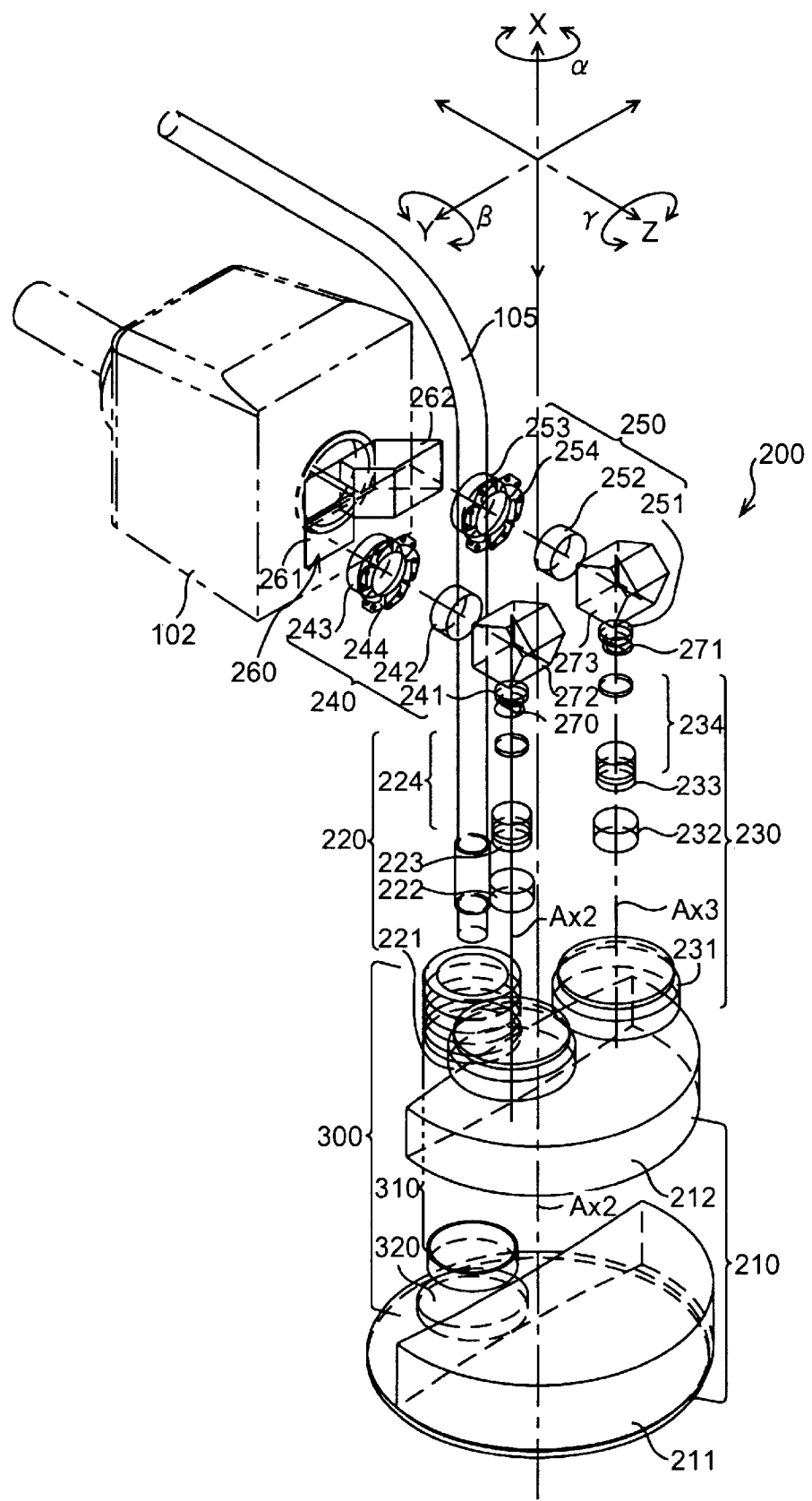
FIG. 6 is a perspective view showing an overall construction of a microscope optical system.
Figure 7:
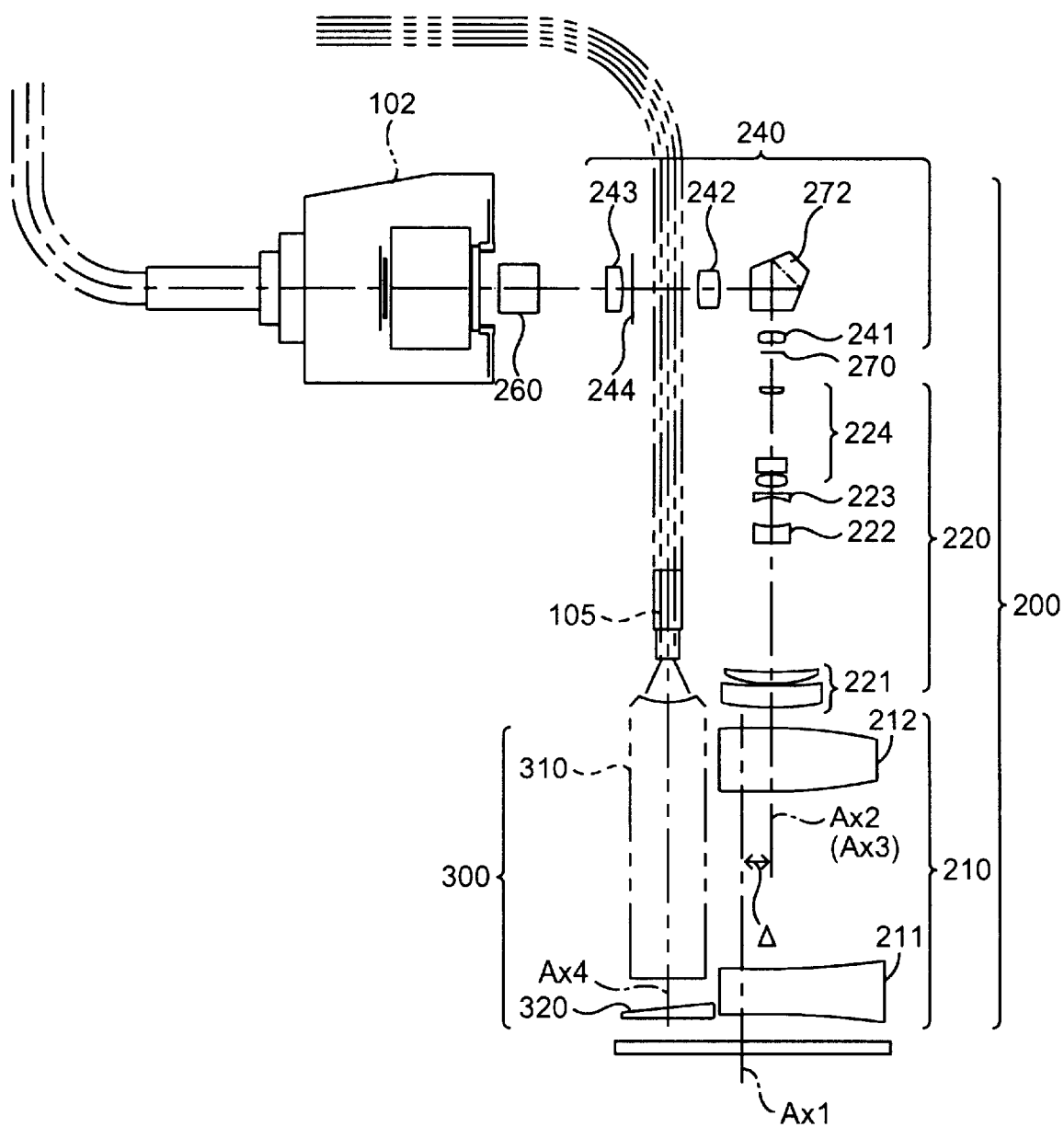
FIG. 7 is a side view showing the overall construction of the microscope optical system.
Figure 8:
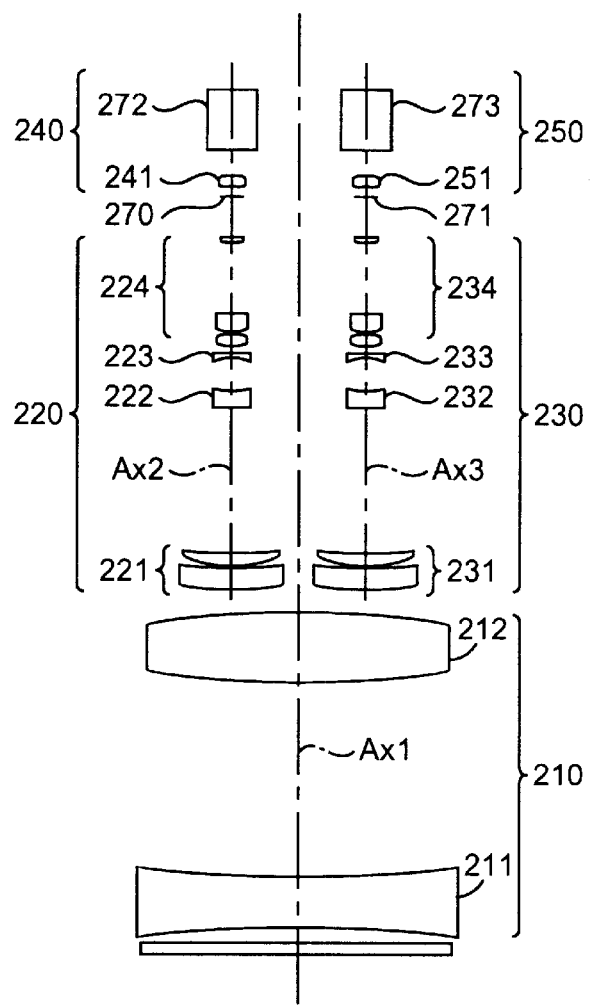
FIG. 8 is a front view showing the overall construction of the microscope optical system.
Figure 9:
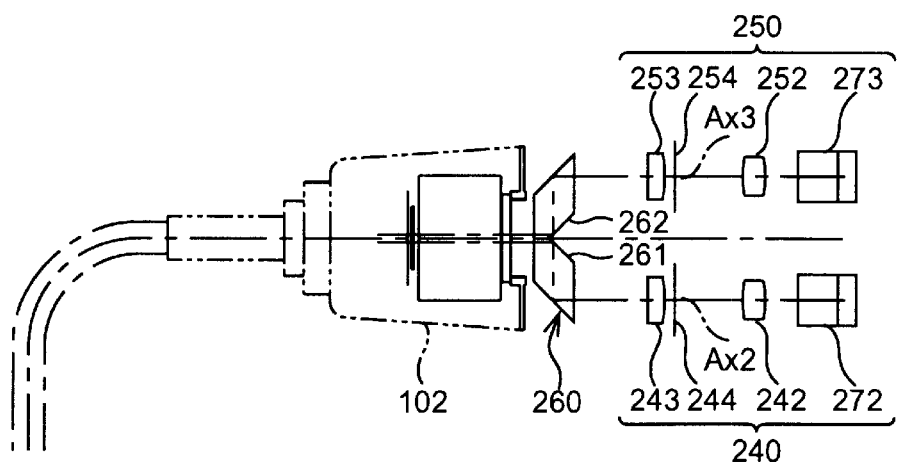
FIG. 9 is a plane view showing the overall construction of the microscope optical system.

Next, the optical configuration of the stereoscopic microscope 101 will be explained with reference to FIGS. 6 through 9. FIG. 6 is a perspective view; FIG. 7 is a side view; FIG. 8 is a front view; and FIG. 9 is a plan view of an overall structure of the microscopic optical system.

As shown in the figures, the microscopic optical system includes an image taking optical system 200 for forming left and right images of an object, an illuminating optical system 300 for illuminating the object with illuminating light guided from the light source 106 through the light guide fiber bundle 105.

The image taking optical system 200 includes an objective optical system, which includes a common close-up optical system 210 and a pair of right and left zoom optical systems 220, 230, for forming the primary images of the object; a pair of right and left relay optical systems 240, 250 for forming the secondary images by relaying the primary images; and an inter-axis distance reducing prism 260 that brings the object light rays from the relay optical systems 240, 250 close to each other. At the positions where the primary images are formed by the zoom optical systems 220, 230, field stops 270, 271 are respectively disposed. In the relay optical systems 240, 250, pentagonal prisms 272, 273 are placed for deflecting the respective light paths at the right angle. According to this construction, right and left images with a predetermined parallax can be formed on adjacent two regions of the CCD 116 installed in the CCD camera 102. Here, in the following explanations of optical systems, "horizontal direction" means the direction that coincides with the longitudinal direction of the image taking surface of the CCD 116 when images are projected thereon, and "vertical direction" means the direction that is perpendicular to the horizontal direction relative to the CCD 116. Each of the optical systems will be explained hereinafter.

As shown in FIGS. 6, 7 and 8, the close-up optical system 210 includes a first lens 211 of a negative refractive power, and a second lens 212 of a positive refractive power arranged in that order from the object side. The second lens 212 moves along its optical axis for focusing in accordance with the object distance. Since the second lens 212 is adjusted so that an object is placed at the object-side focal point of the whole close-up optical system 210, the close-up optical system 210 behaves like a collimator lens to convert divergent light from the object into substantially parallel light. The distance from the vertex of the object-side face of the first lens 211 of the close-up optical system to the object-side focal point of the whole close-up optical system 210 is called "working distance L", which is set to 500+/−100 mm in consideration of focus control region in this embodiment. The plane shape of each of the first and second lenses 211, 212 of the close-up optical system 210, as viewed from the zoom optical systems 220 and 230, is a semicircular shape in which one side is cut out (D-cut). The illuminating optical system 300 is disposed at the cutout portions.

A pair of zoom optical systems 220, 230 focus afocal object light from the close-up optical system 210 at the positions of the field stops 270, 271, respectively.

As shown in FIGS. 6 through 9, the right zoom optical system 220 includes first through fourth lens groups 221, 222, 223 and 224 of positive, negative, negative and positive refractive powers, respectively, in that order from the side of the close-up optical system 210. The first and fourth lens groups 221, 224 are fixed, and the second and third lens groups 222, 223 move for zooming along the optical axis direction. The second lens group 222 moves mainly to change the magnification, and the third lens group 223 moves to maintain the focal position. Like the right zoom optical system 220, the left zoom optical system 230 includes the first through fourth lens groups 231, 232, 233, and 234. The right and left zoom optical systems 220, 230 are interlocked by a driving mechanism (not shown in the figures), whereby the magnifications of the right and left images can be changed simultaneously.

The optical axes Ax2, Ax3 of the zoom optical systems 220, 230 are in parallel with the optical axis Ax1 of the close-up optical system 210. A first plane that includes these optical axes Ax2, Ax3 of the zoom optical systems 220, 230 is offset from a second plane, which is parallel to the first plane and includes the optical axis of the close-up optical system 210, by a distance A at the opposite side of the D-cut portion. The diameter of the close-up optical system 210 is set to be larger than the diameter of a circle that includes the maximum effective diameters of the zoom optical systems 220, 230 and the maximum effective diameter of the illuminating optical system 300. As described above, since the optical axes Ax2, Ax3 of the zoom optical systems 220, 230 are positioned oppositely to the D-cut portion with respect to the optical axis Ax1, the illuminating optical system 300 can be placed inside of a circular region defined by the diameter of the outline shape.

The field stops 270, 271 are disposed at the position where the primary images are formed by the zoom optical systems 220, 230. Each of the field stops 270, 271 has a semi-circular aperture which is concentric with the outer circular edge of the field stop 270, 271 and which is formed at a portion adjacent to the other field stop 271, 270. The straight edges of these apertures coincide with the vertical direction corresponding to the boarder line of the right and left images on the CCD 116. Only flux traveling inside of each of the straight edges can be transmitted.

The microscope according to the present embodiment needs to avoid overlapping of the right and left images on the CCD 116 in order to form the right and left secondary images on adjacent regions of the single CCD 116. Therefore, the field stops 270, 271 are placed at the position of the respective primary images. The straight edge of the semi-circular shaped aperture of each of those field stops 270, 271 functions as a knife-edge, so that only light rays traveling inside the edge can pass through the field stop 270,271. The primary images formed on the field stops 270, 271 are re-imaged through the right and left relay optical systems 240, 250 as secondary images. The resultant secondary images are reversed in the horizontal direction and in the vertical direction with respect to the primary images. Thus, the knife edges defining the outside edges in the horizontal direction at the positions of the primary images define the inside edges in the horizontal directions at the positions of the secondary images, which clearly defines the boundary of the right and left images.

The relay optical systems 240, 250 includes three lens groups of positive refractive powers, respectively. As shown in FIGS. 6 and 7, the right relay optical system 240 includes a first lens group 241 composed of a single positive meniscus lens, a second lens group 242 having a positive refractive power as a whole, and a third lens group 243 composed of a single biconvex lens. The object side focal point of the combination of the first and second lens groups 241 and 242 is coincident with the image forming plane of the primary image formed by the zoom optical system 220. That is the same position as the field stop 271. The third lens group 243 converges parallel light transmitted from the second lens group 242 onto the image taking surface of the CCD 116. Between the first lens group 241 and the second lens group 242, the pentagonal prism 272 is disposed for deflecting the light path at the right angle. Between the second lens group 242 and the third lens group 243, an aperture stop 244 is installed for adjusting the light amount. Like the right relay optical system 240, the left relay optical system 250 includes the first, second and third lens groups 251, 252 and 253. The pentagonal prism 273 is disposed between the first lens group 251 and the second lens group 252, and an aperture stop 254 is installed between the second lens group 252 and the third lens group 253. The divergent light that has passed through the field stops 270, 271 is converted to substantially parallel light through the first lens groups 241, 251 and the second lens groups 242, 252 of the relay optical systems. After passing through the aperture stops 244, 254, the light rays are re-converged through the third lens groups 243, 253 to form the secondary images. Since the pentagonal prisms 272, 273 are disposed inside the relay optical systems 240, 250, the total length of the image taking optical system 200 along the optical axis Ax1 of the close-up optical system 210 can be shortened.

The inter-axis distance reducing prism 260 is disposed between the relay optical systems 240, 250 and the CCD camera 102 to reduce the distance between the right and left object light rays from the respective relay optical systems 240, 250. To attain real stereoscopic feeling by the stereoscopic observation, it is necessary to have a predetermined base length between the right and left zoom optical systems 220, 230 and between the right and left relay optical systems 240, 250. On the other hand, to form secondary images on the adjacent regions on the CCD 116, it is necessary to shorten the distance between the optical axes than the base length. The inter-axis distance reducing prism 260 brings the optical axes of the relay optical systems close to each other, which enables to form secondary images on the same CCD 116 while keeping the predetermined base length. As shown in FIGS. 6 and 9, the inter-axis distance reducing prism 260 includes a pair of optical axis shifting prisms 261, 262 having shapes of the pentagonal columns, which are symmetric to each other. The prisms 261, 262 are arranged in a right and left symmetric configuration with a spacing of about 0.1 mm therebetween.

As shown in FIG. 9, each of the optical axis shifting prisms 261, 262 has incident and exit surfaces that are parallel to each other, and has first and second reflecting surfaces in the respective outer side and inner side, which are also parallel to each other. Viewed in the direction parallel to the incident and exit surfaces and reflecting surfaces, these optical axis shifting prisms 261, 262 have a pentagonal shape formed by cutting out an acute-angle corner of a parallelogram with a line perpendicular to the exit surface.

The object lights from the relay optical systems 240, 250 are incident on the incident surfaces of the respective optical axis shifting prisms 261, 262; internally reflected by the outer reflecting surfaces so as to be directed in the horizontal direction; internally reflected by the inner reflecting surfaces so as to be directed to the optical axis directions that are the same as the incident direction; and are exited from the exit surfaces so as to be incident on the CCD camera 102. As a result, the distance between the right and left object light rays is narrowed without altering the traveling directions, and the secondary images are formed on the single CCD 116.

The illuminating optical system 300 has the function of projecting illumination light onto the object, and, as shown in FIG. 6, includes an illuminating lens 310 for adjusting the degree of divergence of divergent light emitted from the light guide fiber bundle 105 and a wedge prism 320 for deflecting the illumination light to coincide the illuminating region with the image taking region. As shown in FIG. 7, the optical axis Ax4 of the illuminating lens 310 is parallel to the optical axis Ax1 of the close-up optical system 210, and is offset from the optical axis Ax1 by a predetermined amount. Therefore, if the wedge prism 320 is not disposed, the center of the illuminating region would not coincide with the center of the image taking region, which wastes some amount of illuminating light.

Necessity of Antivibration and an Antivibration Mechanism

Figure 10:
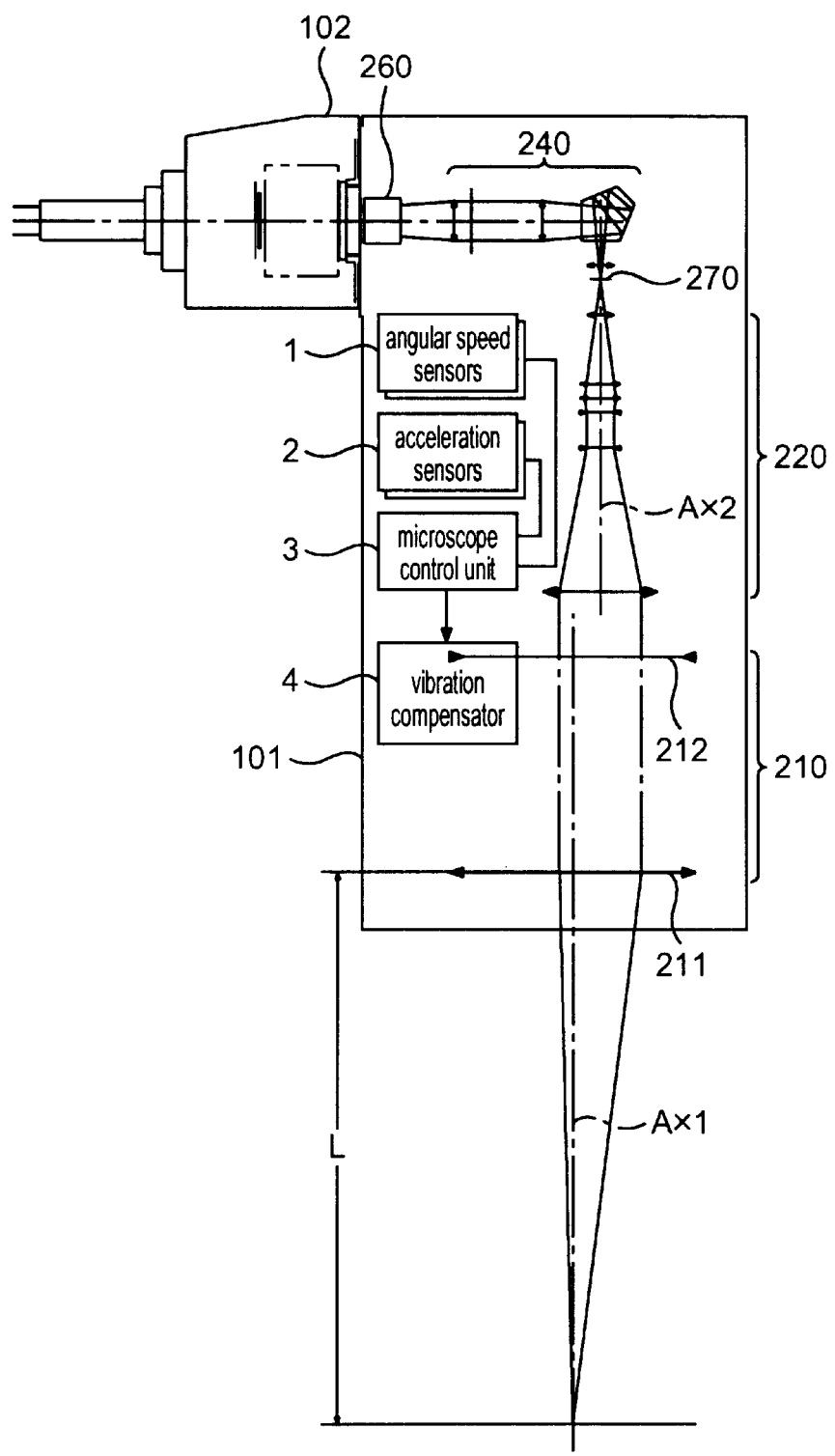
FIG. 10 is a schematic side view showing an antivibration mechanism.
Figure 11:
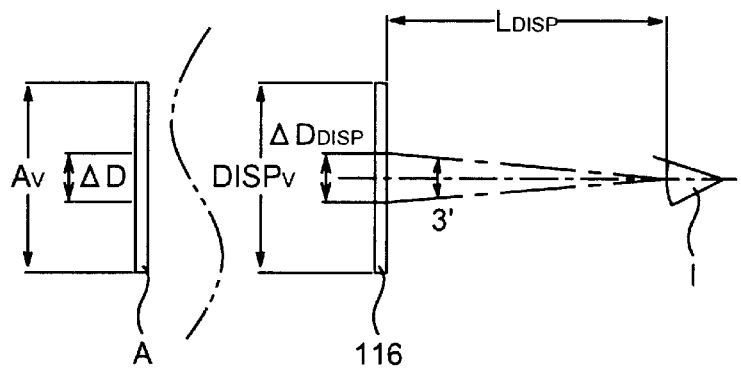
FIG. 11 is an explanatory view for explanation about range antivibration is to be applied.

Now, description will be given of the condition under which the stereoscopic microscope 101 having the above-described basic configuration requires antivibration. Description will be also given of a structure of an antivibration mechanism to be adopted in case the stereoscopic microscope 101 meets such a condition. FIG. 10 schematically shows the antivibration mechanism incorporated into the stereoscopic microscope 101 of the present embodiment. As shown in this FIG. 10, the stereoscopic microscope 101 includes a pair of angular speed sensors 1, a pair of acceleration sensors 2, a microscope control unit 3, and a vibration compensator 4. The microscope control unit 3 is connected to each of the angular speed sensors 1 and each of the acceleration sensors 2. The vibration compensator 4 is connected to the microscope control unit 3.

Here, local coordinate axes in the stereoscopic microscope 101 will be defined with reference to FIG. 6. As shown in FIG. 6, the coordinate axis parallel to the optical axis Ax1 of the close-up optical system 210 is defined as "X axis." The coordinate axis that is orthogonal to the optical axes Ax2 and Ax3 of both the zoom optical systems 220 and 230 is defined as "Y axis." The coordinate axis orthogonal to both the X axis and the Y axis is defined as "Z axis." Moreover, the rotations about the X axis, the Y axis, and the Z axis are defined as "rolling" $\alpha$, "pitching" $\beta$, and "yawing" $\gamma$, respectively.

The above-mentioned angular speed sensors 1 measure the angles of rotation of the stereoscopic microscope 101 in terms of pitching $\beta$ and yawing $\gamma$, respectively, independent of each other. In other words, these angular speed sensors 1 are the first sensors which measure inclination of the whole microscope optical system 200. The above-described acceleration sensors 2 measure the movements of the stereoscopic microscope 101 along the Y axis and the Z axis, respectively, independent of each other. In other words, these acceleration sensors 2 are the second sensors which measure movement of the whole microscope optical system 200. In this connection, the reason why there is provided no angular speed sensor 1 for detecting rotation in terms of rolling α is that the rolling α, even if occurs, creates no change in the direction of the optical axis Ax1 and thus causes no great movement of the field irrespective of the working distance L being long. Similarly, the reason why there is provided no acceleration sensor 2 for detecting a movement along the X axis is that the movement in that direction, even if occurs, creates no change in the direction of the optical axis Ax1 and thus causes no great movement of the field irrespective of the working distance L.

The signals output from these angular speed sensors 1 and acceleration sensors 2 are input to the microscope control unit 3 as a controlling unit. This microscope control unit 3 calculates the direction and angle of the inclination of the stereoscopic microscope 101 (i.e., the inclination of the optical axis Ax1) based on the signals output from the angular speed sensors 1. It also calculates the direction and amount of the shift of this stereoscopic microscope 101 (i.e., the shift within a plane orthogonal to the optical axis Ax1) based on the signals output from the acceleration sensors 2. Then, on the basis of these calculations and the magnification of the microscope optical system 200, the microscope control unit 3 calculates the direction of movement and the amount of movement of an image within the plane including the image taking surface of the CCD 116, which corresponds to the direction of movement and the amount of movement of the field. Then, the vibration compensator 4 is controlled to compensate the direction of movement and the amount of movement of this image so that the image remains stationary on the image taking surface. Now, when the chief operator or other staff moves the stereoscopic microscope 101 with force, it is necessary to disengage clutches which are arranged in the individual hinges of the free arm 100*a* of the first stand 100. Each of the clutches has a sensor for detecting the disengagement and engagement. The microscope control unit 3 stops controlling the vibration compensator whenever any one of the clutch sensors detects clutch disengagement. The microscope control unit 3 restarts controlling the vibration compensator 4 when all the clutch sensors detect clutch engagement.

In the present embodiment, the vibration compensator 4 is a mechanism serving as deflecting device which shifts the second lens 212 of the close-up optical system 210 within a plane orthogonal to the optical axis AX1. It includes actuators for shifting the second lens 212 in the Y direction and the Z direction, respectively. Then, in accordance with the control made by the microscope control unit 3, the vibration compensator 4 drives the individual actuators to shift the second lens 212 so that the traveling direction of a principal ray originated from an object which existed at the center of the field at the point in starting time of the control can be deflected to a direction parallel to the optical axes Ax2 and Ax3 of the zoom optical systems 220 and 230. Thereby, the image formed on the image taking surface of the CCD 116 is fixed as long as the microscope control unit 3 keeps on controlling the vibration compensator 4. Incidentally, when the microscope control unit 3 restarts the control for the vibration compensator 4 after suspension as described above, the vibration compensator 4 may drive the second lens 212 to a neutral position within its shifting range (i.e., a position where it becomes coaxial to the first lens 211).

The antivibration mechanism as described above becomes per se a cause of increases in the weight and cost of the stereoscopic microscope. Therefore, it is undesirable that the antivibration mechanism is incorporated into a stereoscopic microscopes that require no antivibration. Accordingly, description will hereinafter be given of the fact that the stereoscopic microscope 101 in the present embodiment has a necessity for antivibration and of the standards for antivibration. First of all, since the stereoscopic microscope 101 in the present embodiment is intended for surgical operations, with too high magnification or too small field, it is useless in operations. In consideration to the dimensions of the cutting edges of knives, the field is typically set at 15 mm or so in vertical dimention, while the working distance L being 500+/−100 mm.

In general, the optimum distance of observation to see a landscape screen (for example, HDTV screen) is four times the vertical width $DISP_V$ of the screen. Accordingly, an optimum value for the above-mentioned predetermined distance $L_{DISP}$ (hereinafter, referred to as "optimum observation distance") is given by:

$$L_{DISP} = DISP_V \times 4 \quad (1)$$

In other words, in observing the LCD panel 120 of the above-described size, eyes are desirably placed away from the LCD panel 120 by the optical observation distance $L_{DISP}$ given by the foregoing equation (1), for the sake of natural observation. Besides, it is generally considered that human eyes have a resolution of one minute or so in angle because of optic nerve density. Experiments have confirmed, however, that human eyes cannot make recognition of the order of three minutes. Therefore, if an image on the LCD panel 120 spaced away by the optimum observation distance $L_{DISP}$ moves more than three minutes about the observer's eyes, the movement comes to be recognized by the observer, which deteriorates the apparent optical performance of the microscope optical system 200. Accordingly, the maximum amount of movement of the image on the LCD panel 120 which no observer recognizes, or the acceptable amount $\Delta D_{DISP}$ of the image movement is given by:

$$\Delta D_{DISP} = L_{DISP} \times \tan 3' \quad (2)$$
$$= 4 DISP_v \times \tan 3',$$

where an eye resolution is assumed to be approximately three minutes, and $L_{DISP}$ is the optimum observation distance. If a movement of the image on the LCD panel 120 does not exceed $\Delta D_{DISP}$, the movement will not be recognized by the observer who observes from a position away by the optimum observation distance $L_{DISP}$, causing no deterioration in the apparent optical performance.

Meanwhile, as described above, the free arm 100*a* of the first stand 100 is composed of a plurality of arms coupled to one another. Therefore, its swing is relatively greater, which makes it difficult to restrain the amount of linear vibration Δd at the extremity of the free arm 100*a* within 0.04 mm. Given that the amount of linear vibration Δd at the extremity of a 1000 mm-long free arm 100*a* is 0.04 mm, and the free arm 100*a* is fixed at the bottom, then the rotational vibration angle Δω about the bottom is Δω=0.04/1000=8 seconds. Accordingly, it is rather difficult to restrain the rotational vibration angle Δω at the extremity of the free arm 100*a* within 8 seconds. When the extremity of the free arm 100*a* thus makes vibrations (linear motions and rotational vibrations), the stereoscopic microscope 101 also makes vibrations, shaking its optical axis Ax1 so as to move the field. The amount of movement ΔD of the field is expressed as the sum of the amount of movement $\Delta D_{LIN}$ resulting from the linear vibrations of the free arm 100a and the amount of movement $\Delta D_{ROT}$ resulting from the rotational vibrations of the same. This amount of movement $\Delta D_{LIN}$ resulting from the linear vibrations is the amount of linear vibration Δd at the extremity of the free arm 100a. The amount of movement $\Delta D_{ROT}$ resulting from the rotational vibrations coincides with the distance to the field (working distance L) multiplied by the tangent of the vibration angle Δω at the extremity of the free arm 100a (L×tan Δω). Consequently, the amount of movement ΔD of the field is given by the following equation (3):

$$\Delta D = \Delta D_{LIN} + \Delta D_{ROT} \quad (3)$$
$$= \Delta d + L \times \tan\Delta\omega$$
$$= 0.04 + 0.000039 \times L.$$

If the amount of movement of an image on the LCD panel 120 corresponding to the amount of movement AD of the field defined by this equation (3) exceeds the acceptable amount $\Delta D_{DISP}$ defined by the foregoing equation (2), the movement is recognized by the observer with a deterioration in the apparent optical performance. In other words, when the ratio of ΔD to the vertical width ($A_V$) of the field exceeds the ratio of the acceptable amount $\Delta D_{DISP}$ to $DISP_V$, the movement of the image on the LCD panel 120 is recognized by the observer with a deterioration in the apparent optical performance. Hereinafter, "vertical" concerning to the field means the direction corresponding to the vertical direction of the image taking surface of the CCD 116 and therefore, to the vertical direction of the LCD panel 120 which will be orthogonal to interpupillary direction of the chief operator. Accordingly, the necessity to incorporate the antivibration mechanism into the stereoscopic microscope 101 arises when the condition shown by the following expression (4) is satisfied:

$$\Delta D/A_V > \Delta D_{DISP}/DISP_V \quad (4)$$

Modifying this expression (4) into an equation and substituting the foregoing equation (2) into the equation yields:

$$\Delta D/A_V = 4 \times \tan 3'$$
$$1/A_V = 4 \times \tan 3'/\Delta D \quad (5)$$

Substituting the equation (3) into this equation (5) yields:

$$1/A_V = 4 \times \tan 3'/(\Delta d + L \times \tan\Delta\omega) \quad (6)$$
$$= 0.0035/(0.04 + 0.000039 \times L)$$
$$= 1/(11.46 + 0.011 \times L).$$

It is evident from this equation (6) that the threshold of combination of the working distance L and the vertical width $A_V$ of the field at which antivibration is required is expressed as a function of L to the reciprocal of $A_V$. The following Table 1 shows the values of $1/A_V$ calculated by substituting working distances L into this equation (6) in increments of 100.

TABLE 1

| L | $1/A_V$ |
|---|---|
| 100 | 0.081 |
| 200 | 0.075 |
| 300 | 0.069 |
| 400 | 0.064 |
| 500 | 0.060 |
| 600 | 0.056 |
| 700 | 0.053 |
| 800 | 0.050 |
| 900 | 0.047 |
| 1000 | 0.045 |
| 1100 | 0.043 |
| 1200 | 0.041 |
| 1300 | 0.039 |

Figure 12:
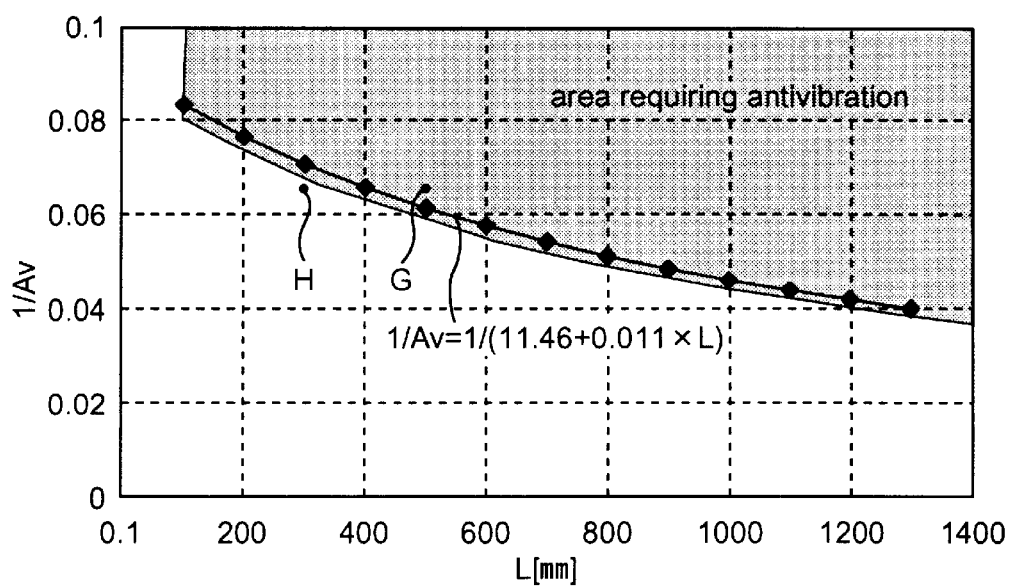
FIG. 12 is a graph showing the range.

FIG. 12 is a graph on which the calculations listed in this Table 1 are plotted to trace the threshold function shown by the foregoing equation (6), with an indication of the area requiring antivibration, i.e., the area given by a modification of the foregoing equation (6) or the following inequality:

$$1/A_V > 1/(11.46 + 0.011 \times L) \quad (6')$$

As shown in FIG. 12, the longer the working distance L is or the shorter the vertical width $A_V$ of the field is (the higher the magnification of the microscope optical system 200 is), the higher the necessity for antivibration becomes. On the contrary, the shorter the working distance L is or the longer the vertical width $A_V$ of the field to be observed is (the lower the magnification of the microscope optical system 200 is), the lower the necessity for antivibration becomes.

The stereoscopic microscope 101 of the present embodiment has a working distance of 500 mm or so, with the vertical width $A_V$ of the field of 15 mm (that is, $1/A_V \approx 0.067$). Therefore, the microscope 101 satisfies the above-mentioned inequality (6'), falling within the area requiring antivibration on the graph shown in FIG. 12, of which position is indicated with the symbol G. Thus, the stereoscopic microscope 101 of the present embodiment needs to incorporate the antivibration mechanism described above. Incidentally, the conventional microscope explained as the related art (of which working distance L=300 mm, and of which vertical width of the field $A_V$=15 mm) falls on the position shown by the symbol H in FIG. 12. This means that the conventional microscope had no need for antivibration originally.

Thus, the present invention has been achieved by examining the rational condition of producing image blur recognizable to observers, and incorporating the antivibration mechanism into a microscope that satisfies the condition. Thus, the microscope having the necessity for antivibration can be surely prevented from image blur.

Incidentally, in the stereoscopic microscope 101 of the present embodiment, only the second lens 212 of the close-up optical system 210 is shifted by the vibration compensator 4. Therefore, the border between the right and left image taking areas on the image taking surface of the CCD 116 will not be split.

Second Embodiment

Figure 13:
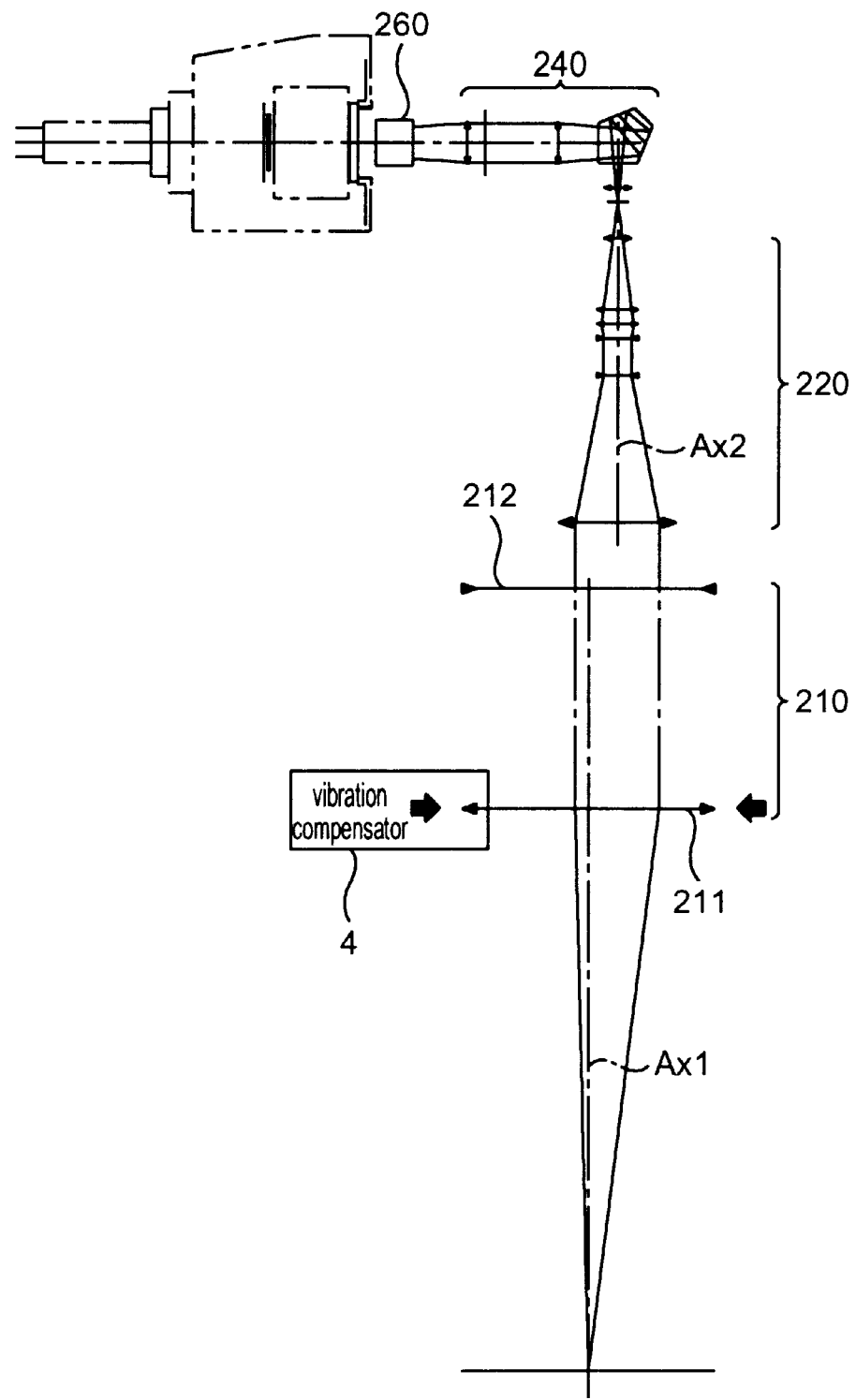
FIG. 13 is a side view showing an overall construction of the microscope optical system in second embodiment of the present invention.
Figure 14:
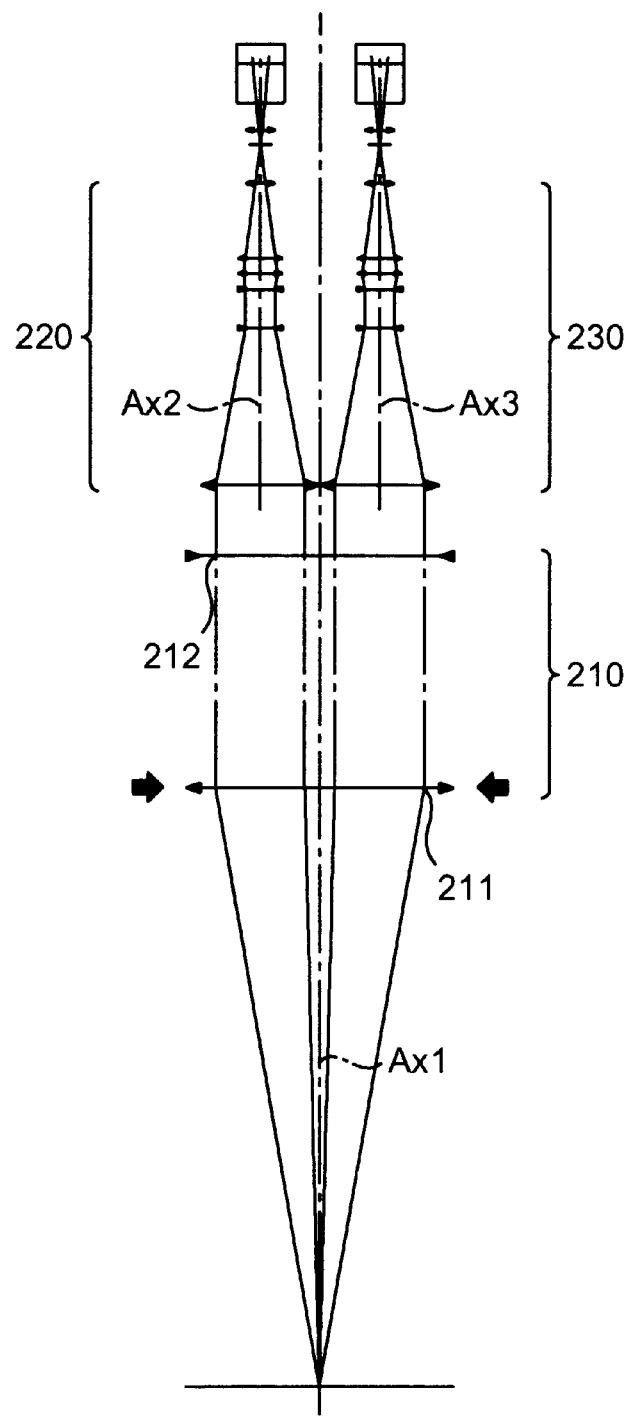
FIG. 14 is a front view showing the overall construction of the microscope optical system in the second embodiment.

A stereoscopic microscope 101 according to a second embodiment of the present invention differs from the stereoscopic microscope 101 according to the first embodiment described above in that the lens to be shifted by the vibration compensator 4 is not the second lens 212 of the close-up optical system 120 but its first lens 211. FIG. 13 is a side view of the microscope optical system 200 in the stereoscopic microscope 101 according to the second embodiment. FIG. 14 is a front view of the same. In these FIGS. 13 and 14, the lens to be shifted (that is, the first lens 211) is indicated with arrows. Even in the case of shifting the first lens 211, the vibration compensator 4 deflects the traveling direction of a principal ray originated from an object which existed at the center on the field at the point in starting time of the control to a direction parallel to the optical axes Ax2 and Ax3 of the zoom optical systems 220 and 230. Thereby, the image of the field formed on the image taking surface of the CCD 116 is fixed as long as the microscope control unit 3 keeps on controlling the vibration compensator 4. Since the other configuration and function of the second embodiment are identical to those of the foregoing first embodiment, description thereof will be omitted here.

Third Embodiment

Figure 15:
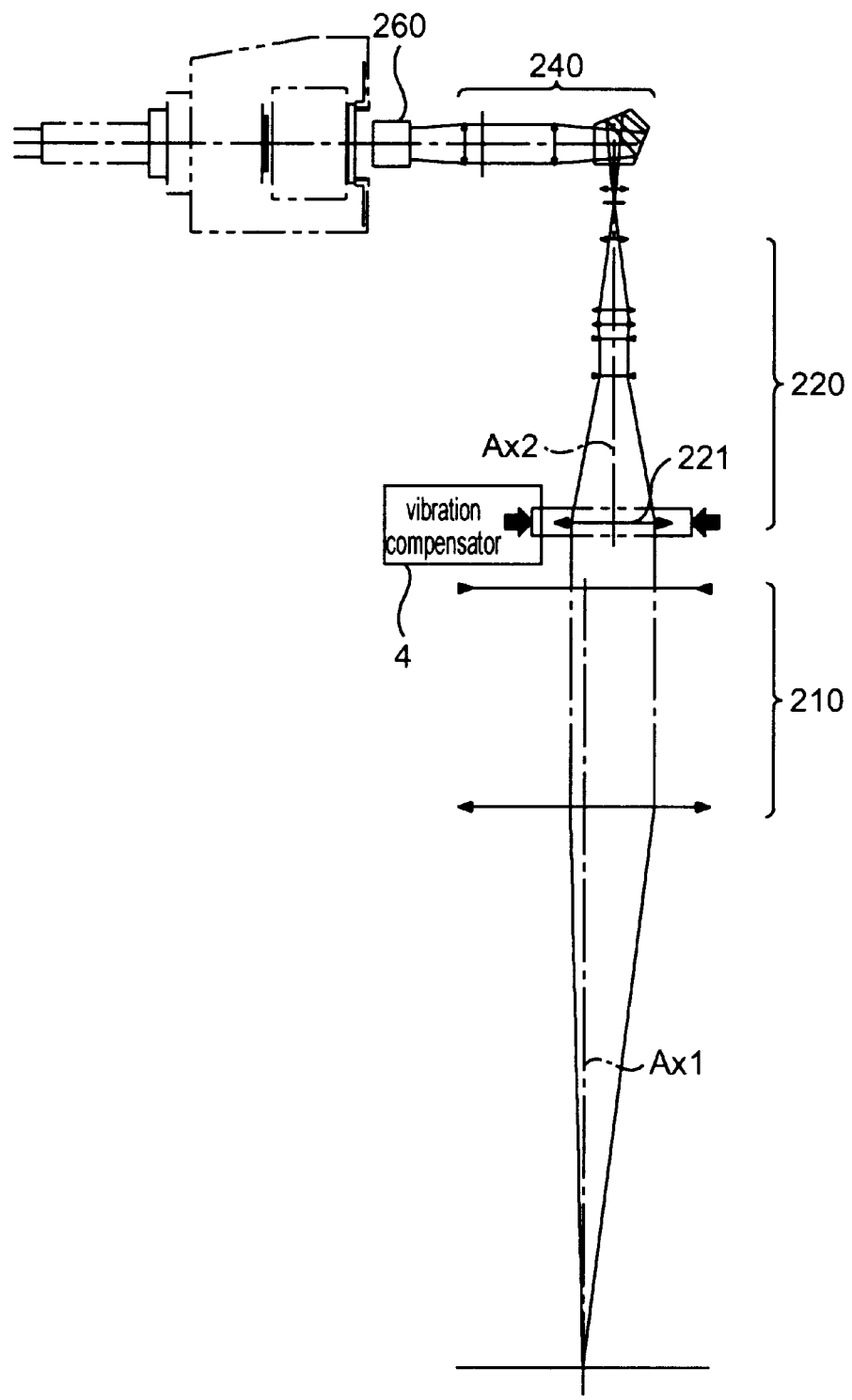
FIG. 15 is a side view showing an overall construction of the microscope optical system in third embodiment of the present invention.
Figure 16:
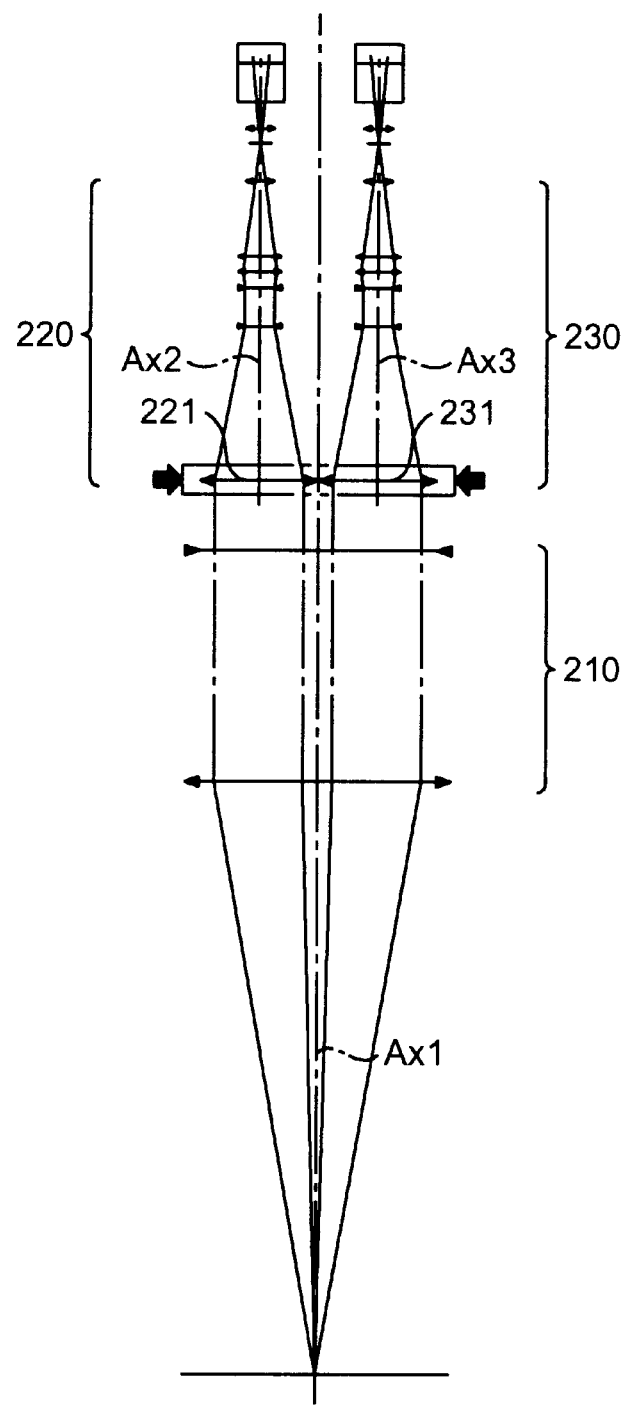
FIG. 16 is a front view showing the overall construction of the microscope optical system in the third embodiment.

A stereoscopic microscope 101 according to a third embodiment of the present invention differs from the stereoscopic microscope 101 according to the first embodiment described above in that the lenses to be shifted by the vibration compensator 4 are the first lens groups 221, 231, which are fixed during zooming, of the zoom optical systems 220, 230. FIG. 15 is a side view of the microscope optical system 200 in the stereoscopic microscope 101 according to the third embodiment. FIG. 16 is a front view of the same. In these FIGS. 15 and 16, the lens groups to be shifted (that is, the first lens groups 221, 231) are indicated with arrows. Even in the case of shifting the first lens groups 221, 231, the vibration compensator 4 deflects the traveling direction of a principle ray originated from an object which existed at the center of the field at the point in starting time of the control to a direction parallel to the optical axes Ax2, Ax3 of the zoom optical systems 220 and 230. Thereby, the image of the field formed on the image taking surface of the CCD 116 is fixed as long as the microscope control unit 3 keeps on controlling the vibration compensator 4. Since the other configuration and function of the third embodiment are identical to those of the foregoing first embodiment, description thereof will be omitted here.

Fourth Embodiment

Figure 17:
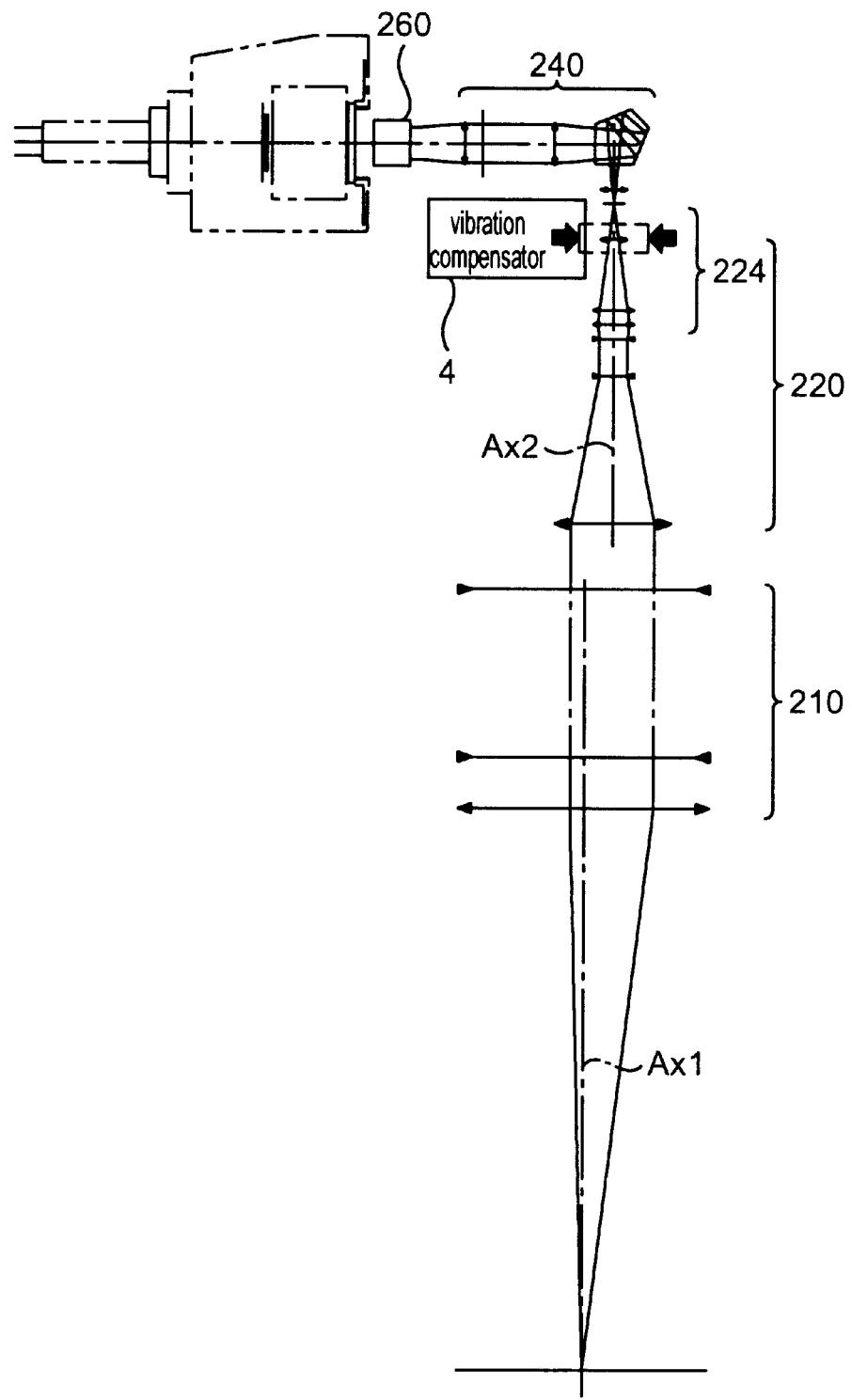
FIG. 17 is a side view showing an overall construction of the microscope optical system in fourth embodiment of the present invention.
Figure 18:
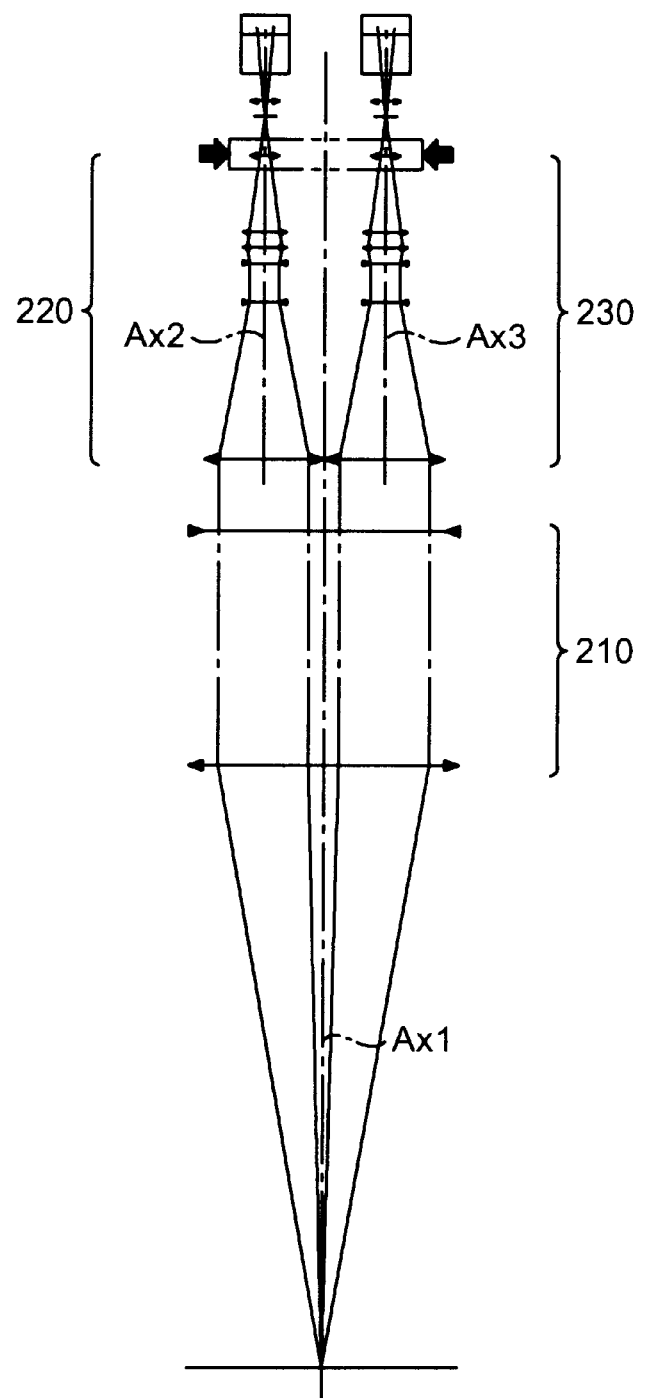
FIG. 18 is a front view showing the overall construction of the microscope optical system in the fourth embodiment.

A stereoscopic microscope 101 according to a fourth embodiment of the present invention differs from the stereoscopic microscope 101 according to the first embodiment described above in that the lenses to be shifted by the vibration compensator 4 are the final lenses of the fourth lens groups 224, 234, which are fixed during zooming, of the zoom optical systems 220, 230. FIG. 17 is a side view of the microscope optical system 200 in the stereoscopic microscope 101 according to the fourth embodiment. FIG. 18 is a front view of the same. In these FIGS. 17 and 18, the lens groups to be shifted (that is, the final lenses of the fourth lens groups 224, 234) are indicated with arrows. Even in the case of shifting the final lenses of the fourth lens groups 224, 234, the vibration compensator 4 deflects the traveling direction of a principal ray originated from an object which existed at the center of the field at the point in starting time of the control to a direction parallel to the optical axes Ax2, Ax3 of the zoom optical systems 220 and 230. Thereby, the image of the field formed on the image taking surface of the CCD 116 is fixed as long as the microscope control unit 3 keeps on controlling the vibration compensator 4. Since the other configuration and function of the fourth embodiment are identical to those of the foregoing first embodiment, description thereof will be omitted here.

Fifth Embodiment

Figure 19:
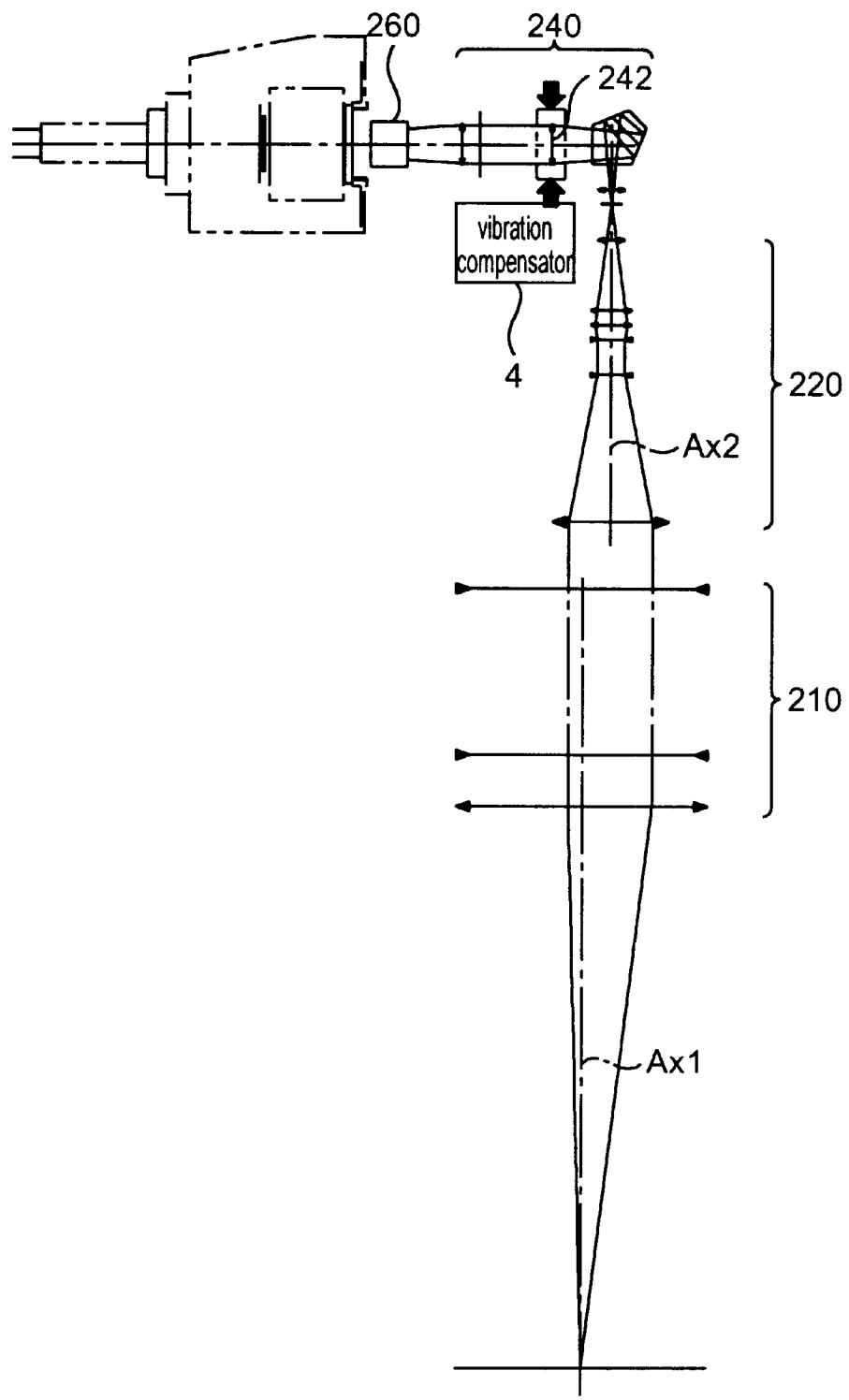
FIG. 19 is a side view showing an overall construction of the microscope optical system in fifth embodiment of the present invention.
Figure 20:
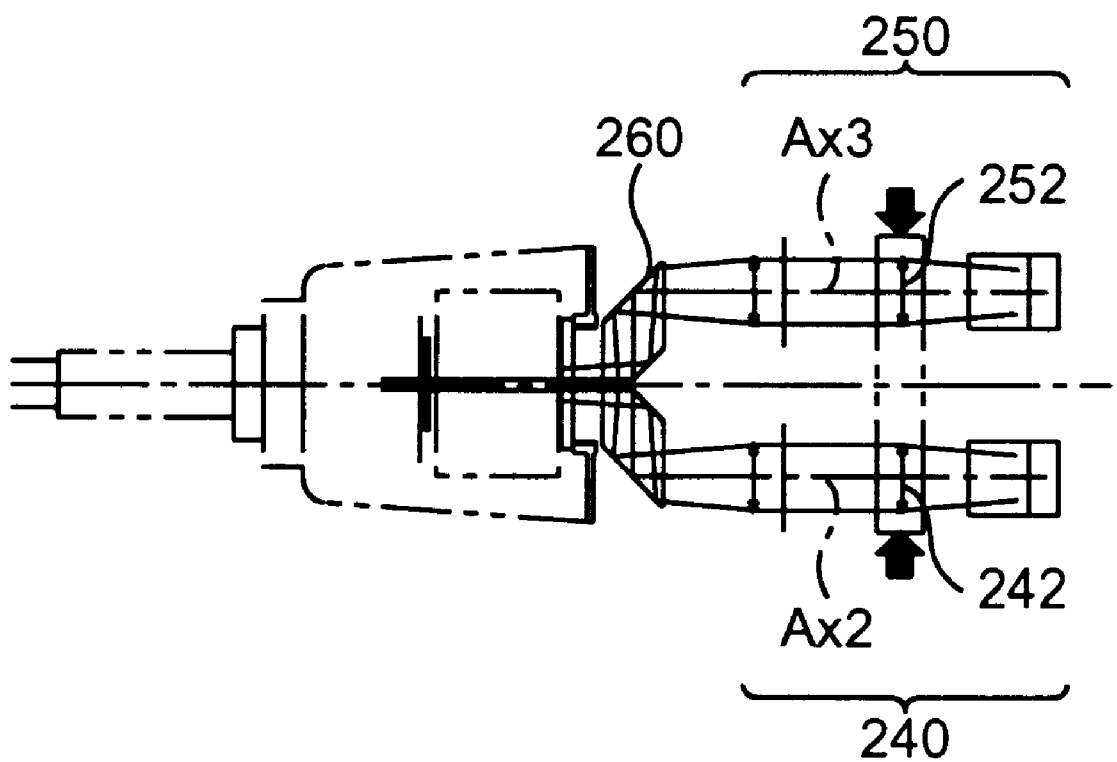
FIG. 20 is a plane view showing the overall construction of the microscope optical system in the fifth embodiment.

A stereoscopic microscope 101 according to a fifth embodiment of the present invention differs from the stereoscopic microscope 101 according to the first embodiment described above in that the lenses to be shifted by the vibration compensator 4 are the second lens groups 242, 252 of the relay optical systems 240, 250. FIG. 19 is a side view of the microscope optical system 200 in the stereoscopic microscope 101 according to the fifth embodiment. FIG. 20 is a front view of the same. In these FIGS. 19 and 20, the lens groups to be shifted (that is, the second lens groups 242, 252) are indicated with arrows. Even in the case of shifting the second lens groups 242, 252, the vibration compensator 4 deflects the traveling direction of a principal ray originated from an object which existed at the center of the field at the point in starting time of the control to a direction parallel to the optical axes Ax2, Ax3 of the relay optical systems 240 and 250. Thereby, the image of the field formed on the image taking surface of the CCD 116 is fixed as long as the microscope control unit 3 keeps on controlling the vibration compensator 4. In this fifth embodiment, the lenses to be shifted by the vibration compensator 4 are the second lens groups 242, 252 of the relay optical systems 240, 250 which have small diameter and therefore light weight, so that road tasking the vibration compensator 4 can be reduced. Since the other configuration and function of the fifth embodiment are identical to those of the foregoing first embodiment, description thereof will be omitted here.

Sixth Embodiment

Figure 21:
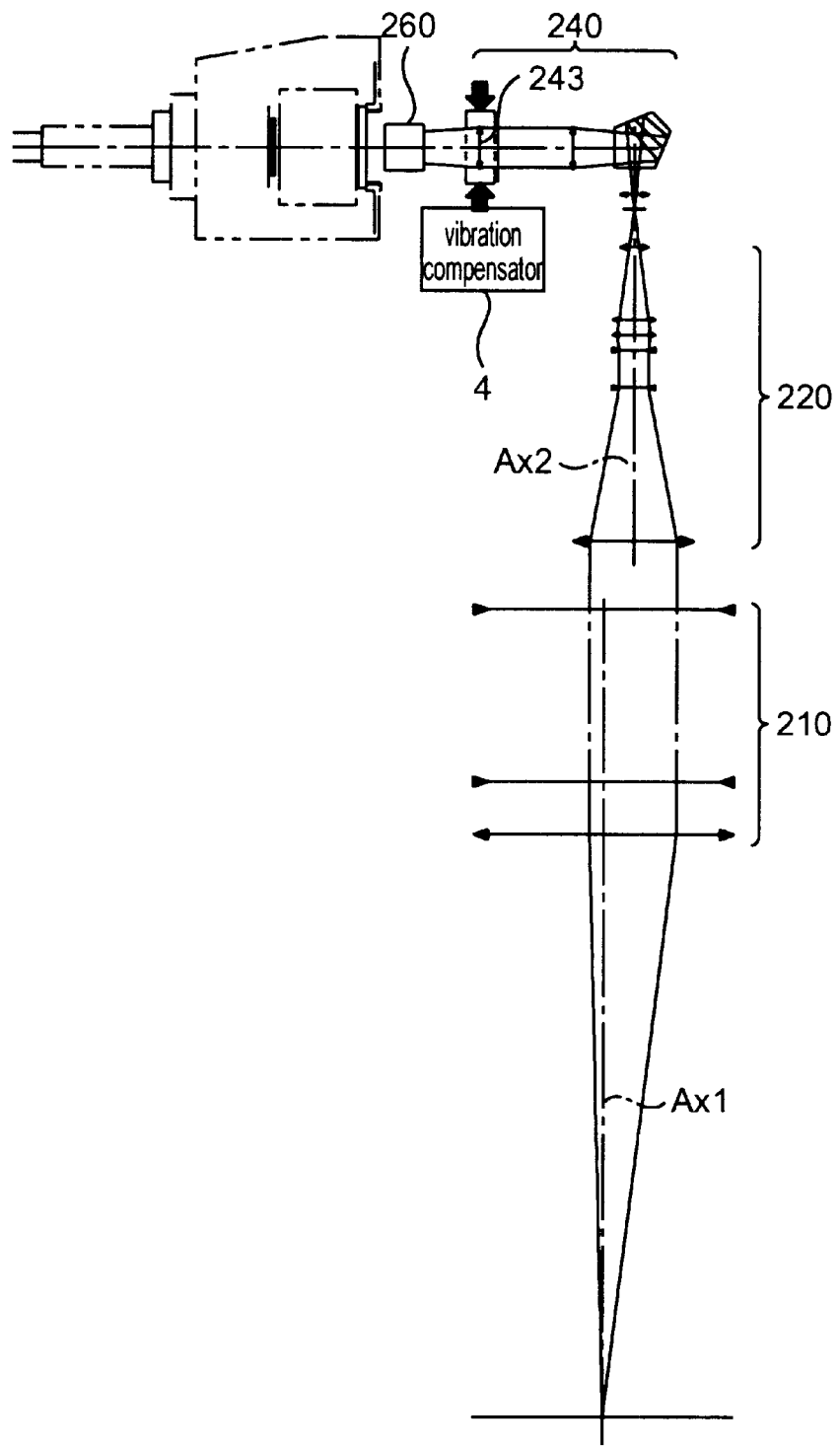
FIG. 21 is a side view showing an overall construction of the microscope optical system in sixth embodiment of the present invention.
Figure 22:
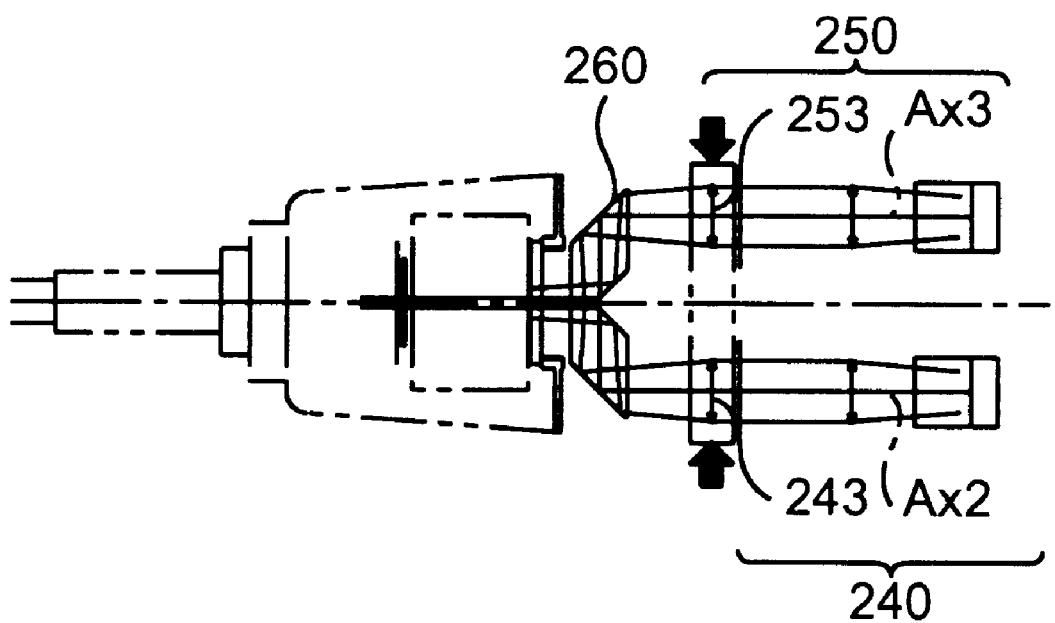
FIG. 22 is a plane view showing the overall construction of the microscope optical system in the sixth embodiment.

A stereoscopic microscope 101 according to a sixth embodiment of the present invention differs from the stereoscopic microscope 101 according to the first embodiment described above in that the lens to be shifted by the vibration compensator 4 is not the second lens 212 of the close-up optical system 120 but the third lens groups 243, 253 of the relay optical systems 240, 250. FIG. 21 is a side view of the microscope optical system 200 in the stereoscopic microscope 101 according to the sixth embodiment. FIG. 22 is a front view of the same. In these FIGS. 21 and 22, the lens groups to be shifted (that is, the third lens groups 243, 253) are indicated with arrows. Even in the case of shifting the second lens groups 243, 253, the vibration compensator 4 deflects the traveling direction of object light originated from the field at the point of starting control to a direction parallel to the optical axes Ax2, Ax3 of the relay optical systems 240 and 250. Thereby, the image of the field formed on the image taking surface of the CCD 116 is fixed as long as the microscope control unit 3 keeps on controlling the vibration compensator 4. In this sixth embodiment, the lenses to be shifted by the vibration compensator 4 are the third lens groups 243, 253 of the relay optical systems 240, 250 which have small diameter and therefore light weight, so that road tasking the vibration compensator 4 can be reduced. Since the other configuration and function of the sixth embodiment are identical to those of the foregoing first embodiment, description thereof will be omitted here.

In the first through sixth embodiments described above, the lenses constituting the microscope optical system 200 shown in FIGS. 6 through 10 are shifted. Alternatively, an optical system dedicated to shifting an optical axis, including a plurality of lenses having powers negating one another may be inserted into the microscope optical system 200 so that some of the lenses constituting this optical system may be shifted.

Seventh Embodiment

Seventh through tenth embodiments of the present invention are examples where a reflecting mirror for bending an optical axis or optical axes at right angle is inserted into the microscope optical system 200, and the vibration compensator 4 adjusts the direction of inclination and the angle of inclination of this reflecting mirror so that object light from the field may be deflected to a direction parallel to the optical axes Ax2, Ax3.

Figure 23:
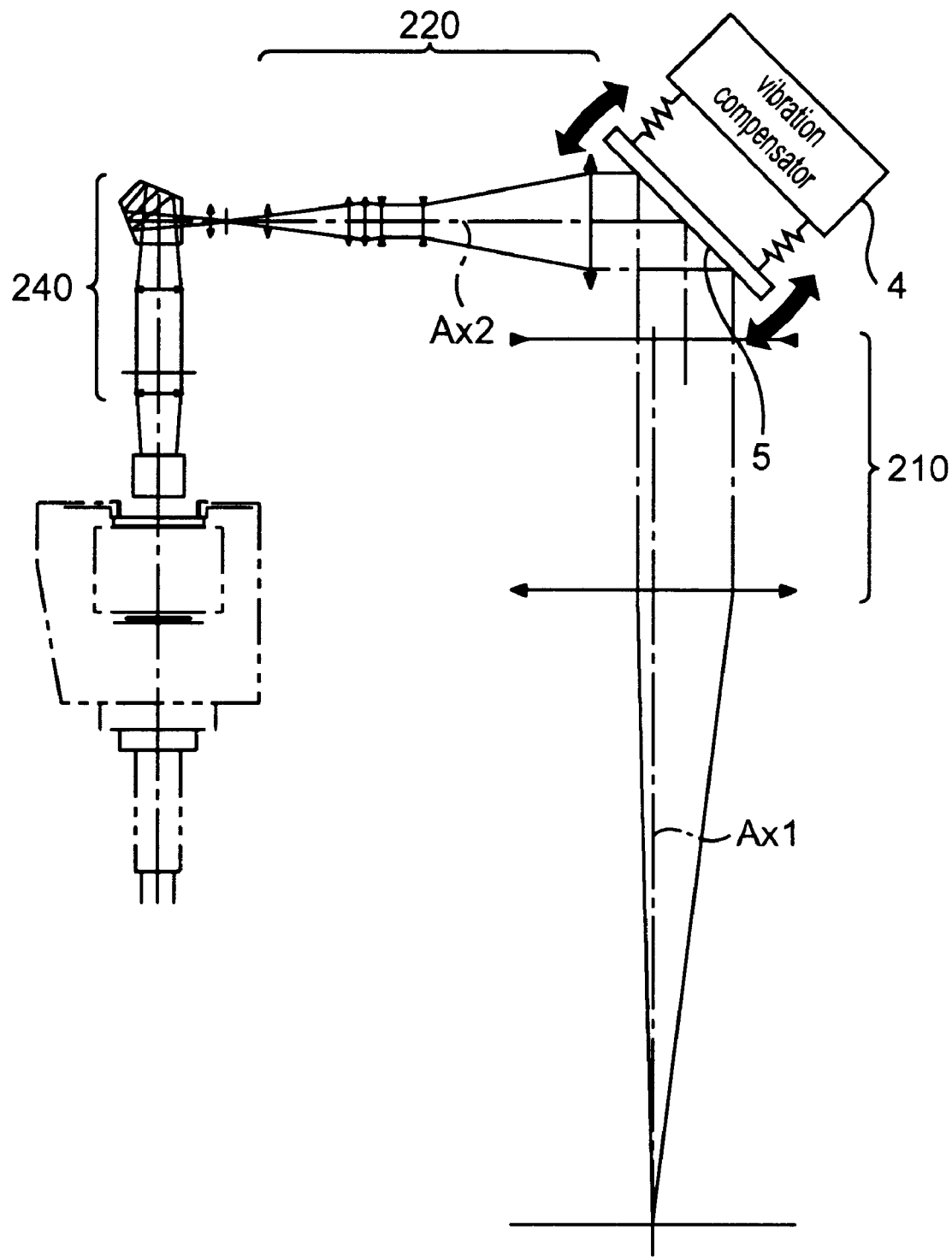
FIG. 23 is a side view showing an overall construction of the microscope optical system in seventh embodiment of the present invention.
Figure 24:
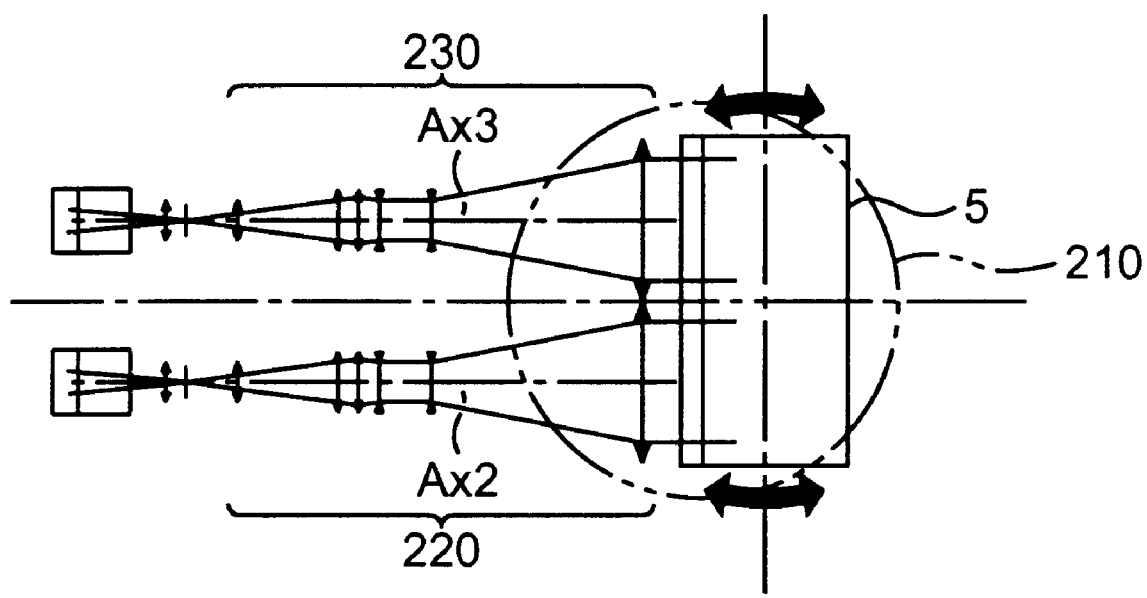
FIG. 24 is a plane view showing the overall construction of the microscope optical system in the seventh embodiment.

The seventh embodiment is an example where a single reflecting mirror 5 for bending the optical axis Ax1 of the close-up optical system 210 and the optical axes Ax2, Ax3 of the zoom optical systems 220, 230 at right angle is inserted between the close-up optical system 210 and the zoom optical systems 220, 230. FIG. 23 is a side view of the microscope optical system 200 in the stereoscopic microscope 101 according to the seventh embodiment. FIG. 24 is a plan view of the same. In the seventh embodiment, the vibration compensator 4 has actuators at several points around the center of back of the reflecting mirror 5. These actuators holds the reflecting mirror 5 such that they are capable of pushing and pulling. Then, the vibration compensator 4 can push/pull the back of the reflecting mirror 5 with the individual actuators as appropriate, so as to incline this reflecting mirror 5 to arbitrary direction at arbitrary angle. The vibration compensator 4 inclines the reflecting mirror 5 in accordance with the control made by the microscope control unit 3, so that an principal ray originating from an object which existed at the center of the field at the point in starting time of the control is deflected to a direction parallel to the optical axes Ax2 and Ax3 of the zoom optical systems 220 and 230. Thereby, the image of the field formed on the image taking surface of the CCD 116 is fixed as long as the microscope control unit 3 keeps on controlling the vibration compensator 4. In the present embodiment, only a single piece of reflecting mirror 5 is sufficient. Therefore, the vibration compensator 4 may have a relatively simple structure. Since the other configuration and function of the seventh embodiment are identical to those of the foregoing first embodiment, description thereof will be omitted here.

Incidentally, in the seventh embodiment, the reflecting mirror 5 may be replaced with a triangular prism in which incident light is internally reflected by its oblique face to be emitted therefrom.

Eighth Embodiment

Figure 25:
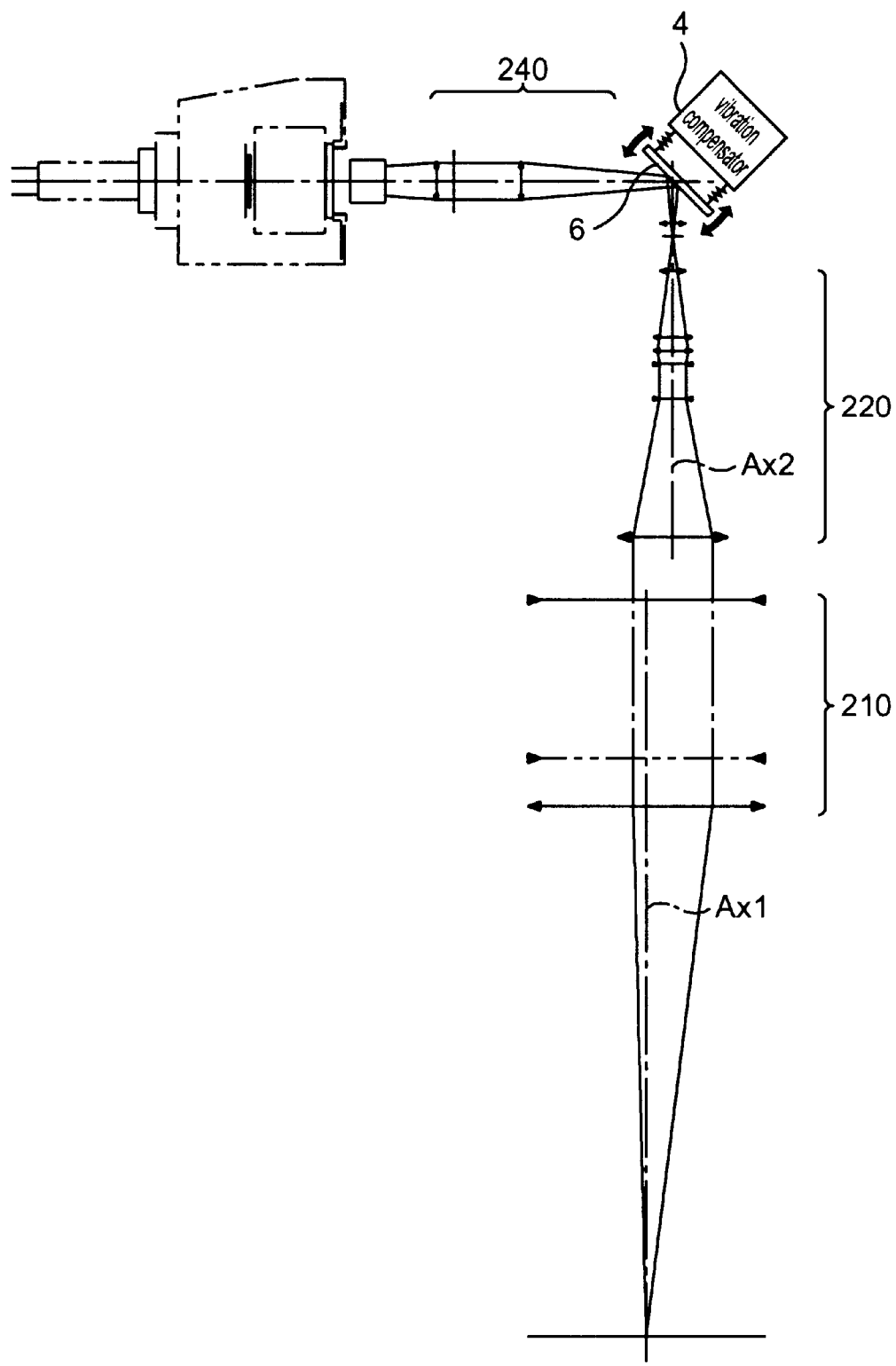
FIG. 25 is a side view showing an overall construction of the microscope optical system in eighth embodiment of the present invention.
Figure 26:
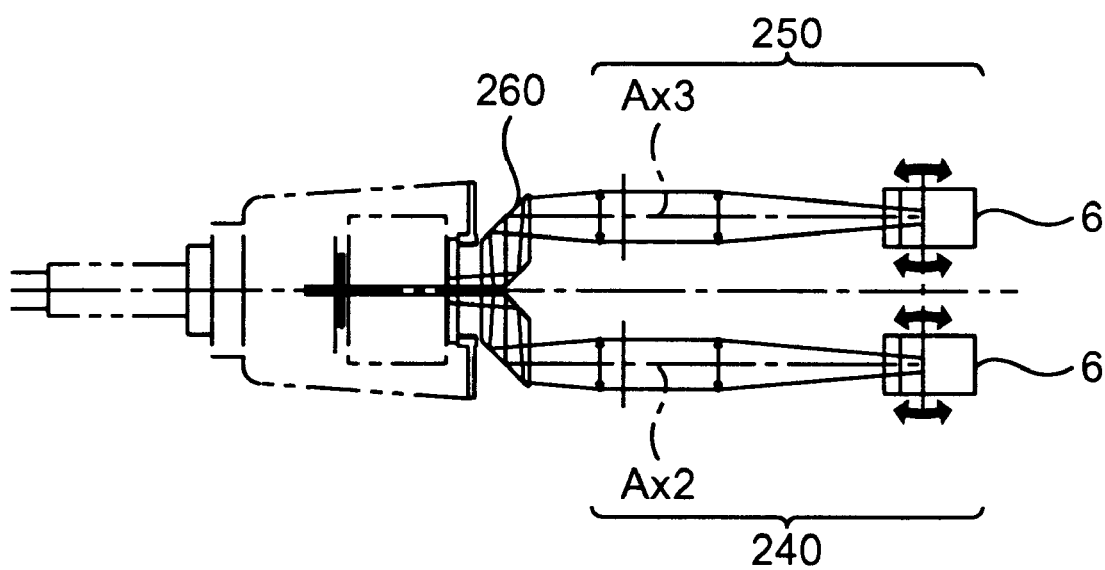
FIG. 26 is a plane view showing the overall construction of the microscope optical system in the eighth embodiment.

The eighth embodiment is an example where a pair of reflecting mirrors 6, 6 which can be adjusted in inclination angle and inclination direction by the vibration compensator 4 instead of the pentagonal prisms 272, 273 shown in FIGS. 6 through 10. FIG. 25 is a side view of the microscope optical system 200 in the stereoscopic microscope 101 according to the eighth embodiment. FIG. 26 is a plan view of the same. In the eighth embodiment, a pair of the vibration compensators 4, 4 are provided to the reflecting mirrors 6, 6, respectively. Each of the vibration compensators 4, 4 has the same structure as the seventh embodiment described above to incline its corresponding reflecting mirrors 6, 6 in arbitrary direction at arbitrary angle. The vibration compensators 4, 4 incline the reflecting mirrors 6, 6 in accordance with the control made by the microscope control unit 3, so that a principal ray originating from an object which existed at the center of the field at the point in starting time of the control is deflected to a direction parallel to the optical axes Ax2 and Ax3 of the relay optical systems 240 and 250. Thereby, the image of the field formed on the image taking surface of the CCD 116 is fixed as long as the microscope control unit 3 keeps on controlling the vibration compensators 4, 4. Since the other configuration and function of the eighth embodiment are identical to those of the foregoing first embodiment, description thereof will be omitted here.

Incidentally, in the eighth embodiment, the reflecting mirrors 6, 6 may be replaced with a triangular prism in which incident light is internally reflected by its oblique face to be emitted therefrom.

Ninth Embodiment

Figure 27:
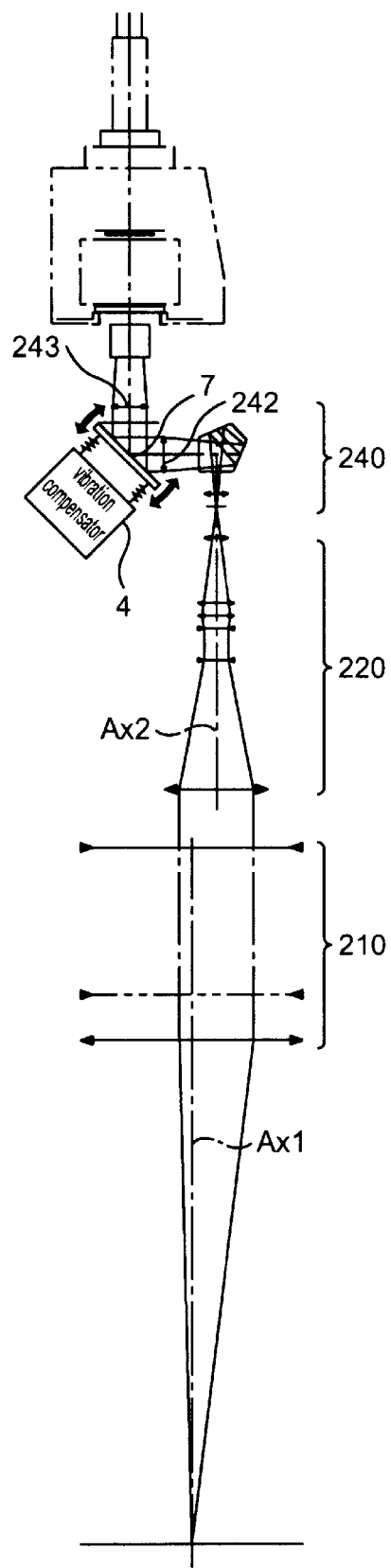
FIG. 27 is a side view showing an overall construction of the microscope optical system in ninth embodiment of the present invention.
Figure 28:
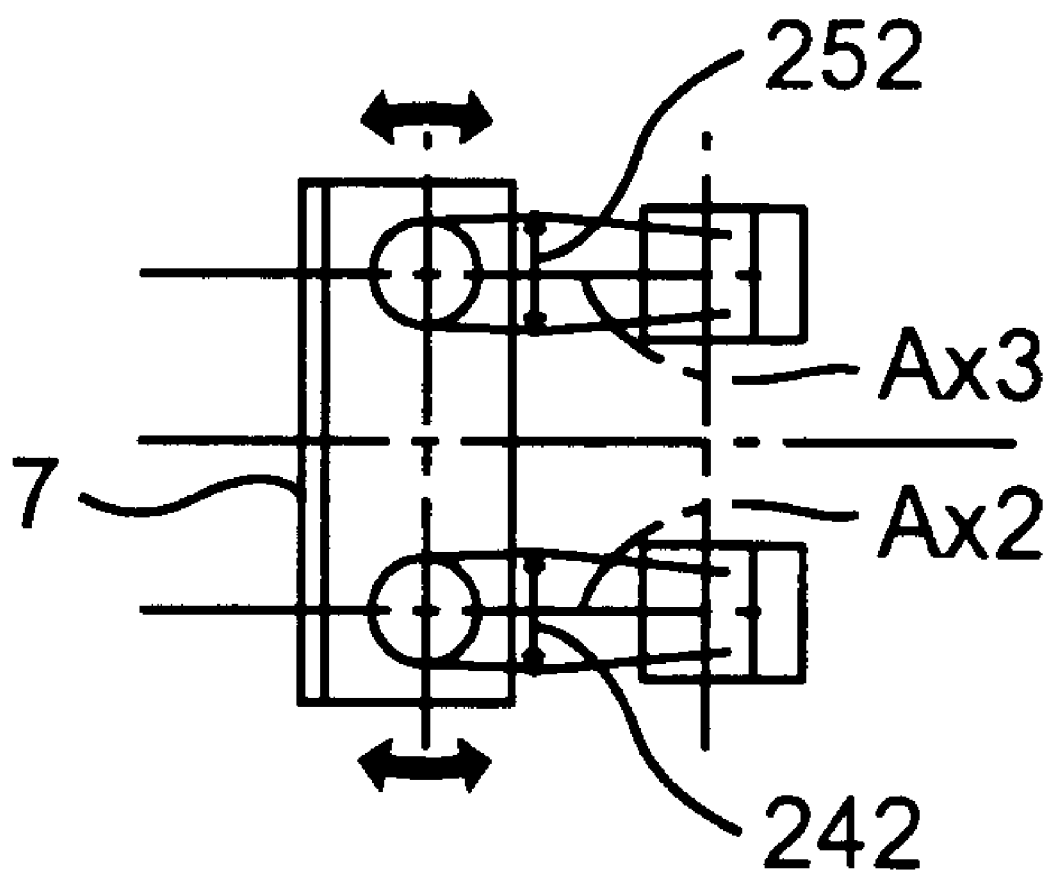
FIG. 28 is a plane view showing the overall construction of the microscope optical system in the ninth embodiment.

The ninth embodiment is an example where a single reflecting mirror 7 for bending the optical axes Ax2, Ax3 of the relay optical systems 240, 250 at right angle is inserted between the second lenses 242, 252 and the third lenses 243, 253 of the individual relay optical systems 240, 250. FIG. 27 is a side view of the microscope optical system 200 in the stereoscopic microscope 101 according to the ninth embodiment. FIG. 28 is a plan view of the same. The vibration compensator 4 has the same structure as the seventh embodiment described above to incline the reflecting mirror 7 in arbitrary direction at arbitrary angle. The vibration compensator 4 inclines the reflecting mirrors 7 in accordance with the control made by the microscope control unit 3, so that a principal ray originating from an object which existed at the center of the field at the point in starting time of the control is deflected to a direction parallel to the optical axes Ax2 and Ax3 of the relay optical systems 240 and 250. Thereby, the image of the field formed on the image taking surface of the CCD 116 is fixed as long as the microscope control unit 3 keeps on controlling the vibration compensator 4. Since the other configuration and function of the ninth embodiment are identical to those of the foregoing first embodiment, description thereof will be omitted here.

Incidentally, in the ninth embodiment, the reflecting mirror 7 may be replaced with a triangular prism in which incident light is internally reflected by its oblique face to be emitted therefrom.

Tenth Embodiment

Figure 29:
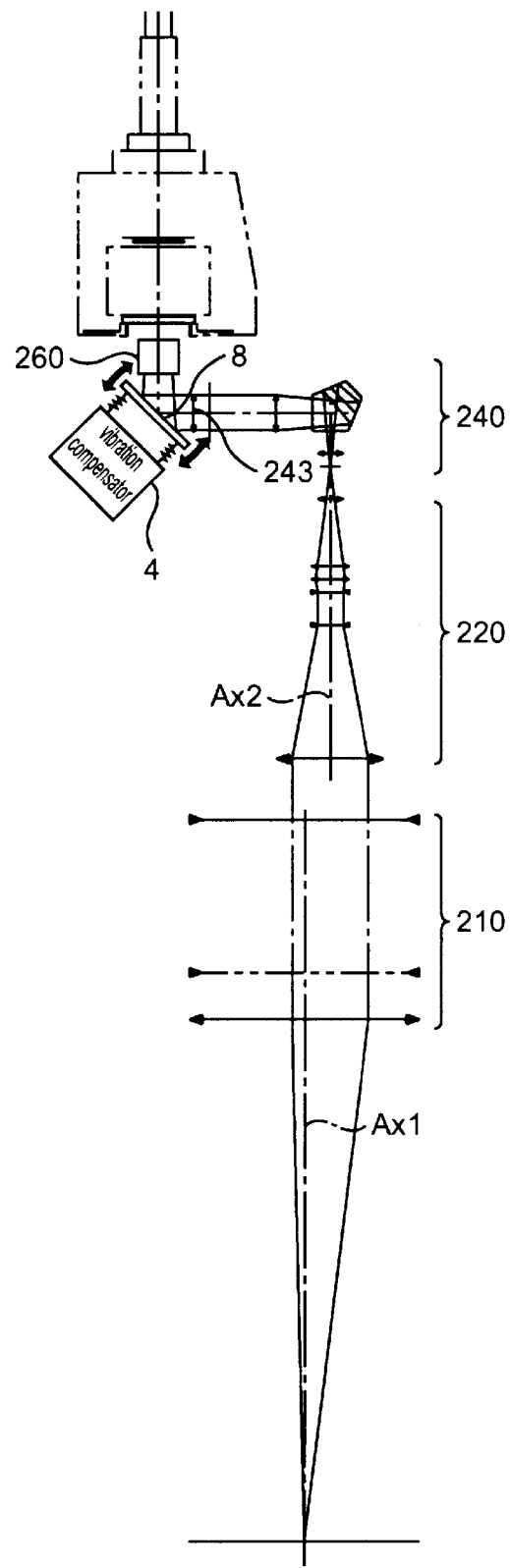
FIG. 29 is a side view showing an overall construction of the microscope optical system in tenth embodiment of the present invention.
Figure 30:
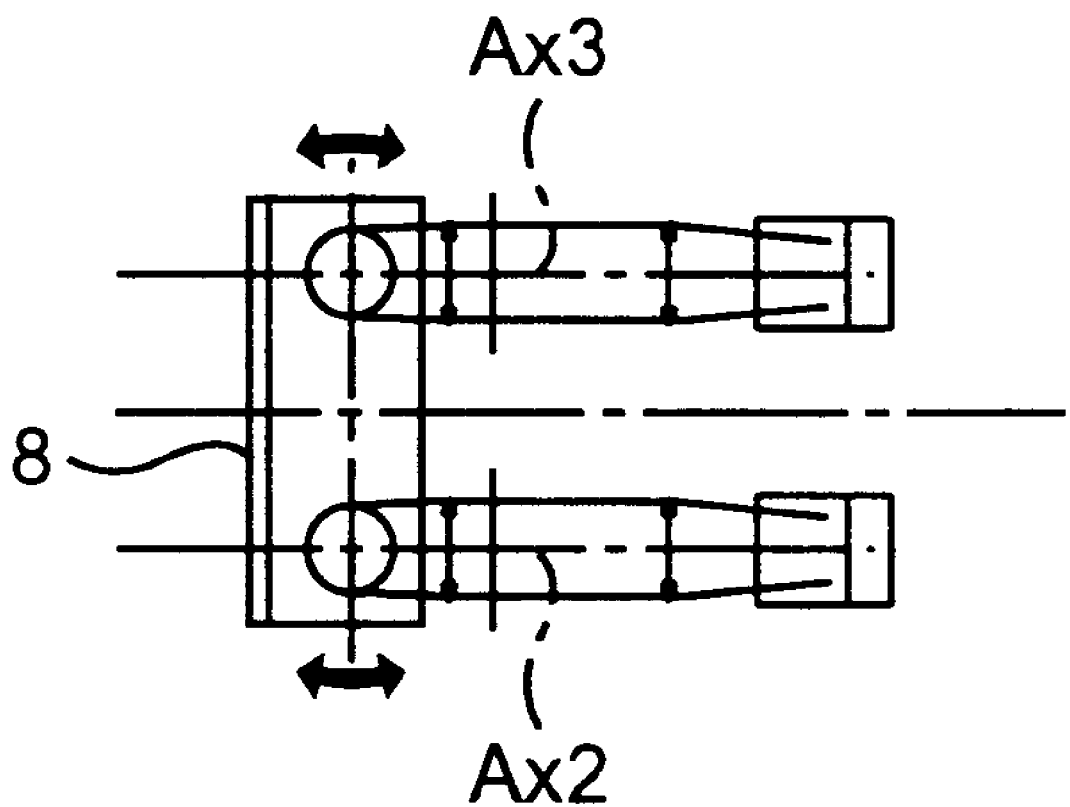
FIG. 30 is a plane view showing the overall construction of the microscope optical system in the tenth embodiment.

The tenth embodiment is an example where a single reflecting mirror 8 for bending the optical axes Ax2, Ax3 of the relay optical systems 240, 250 at right angle is inserted between the individual relay optical systems 240, 250 and the inter-axis distance reducing prism 260, which cranks the optical axes Ax2, Ax3 as a whole. FIG. 29 is a side view of the microscope optical system 200 in the stereoscopic microscope 101 according to the tenth embodiment. FIG. 30 is a plan view of the same. The vibration compensator 4 has the same structure as the seventh embodiment described above to incline the reflecting mirror 8 in arbitrary direction at arbitrary angle. The vibration compensator 4 inclines the reflecting mirror 8 in accordance with the control made by the microscope control unit 3, so that a principal ray originating from an object which existed at the center of the field at the point in starting time of the control is deflected to a direction parallel to the optical axes Ax2 and Ax3 of the relay optical systems 240 and 250. Thereby, the image of the field formed on the image taking surface of the CCD 116 is fixed as long as the microscope control unit 3 keeps on controlling the vibration compensator 4. Since the other configuration and function of the tenth embodiment are identical to those of the foregoing first embodiment, description thereof will be omitted here.

Incidentally, in the tenth embodiment, the reflecting mirrors 8 may be replaced with a triangular prism in which incident light is internally reflected by its oblique face to be emitted therefrom.

Eleventh Embodiment

Figure 31:
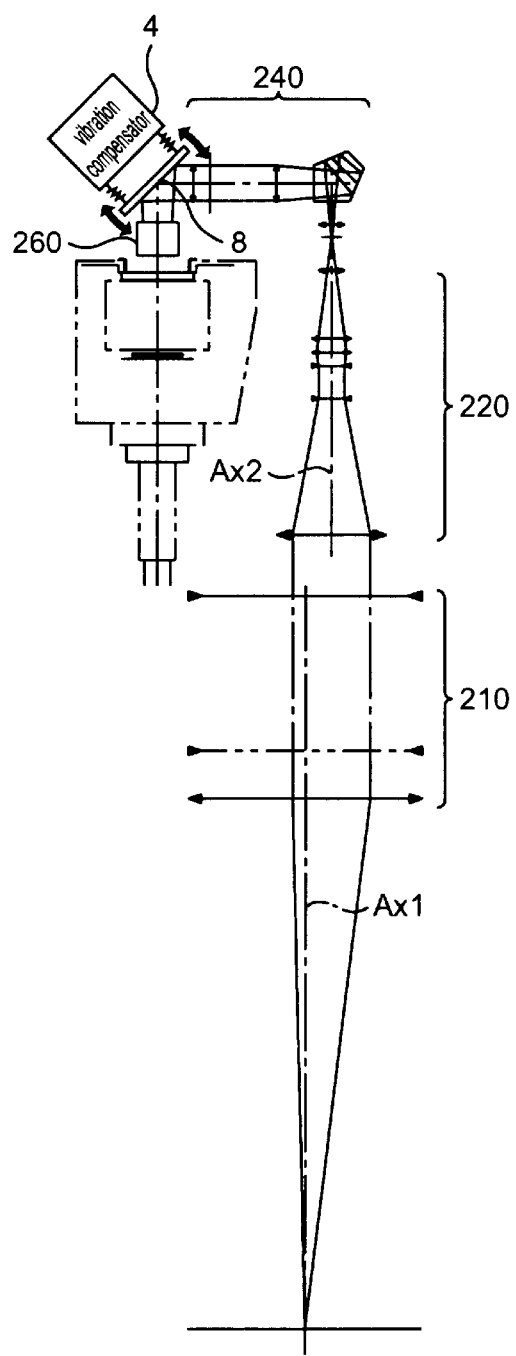
FIG. 31 is a side view showing an overall construction of the microscope optical system in eleventh embodiment of the present invention.
Figure 32:
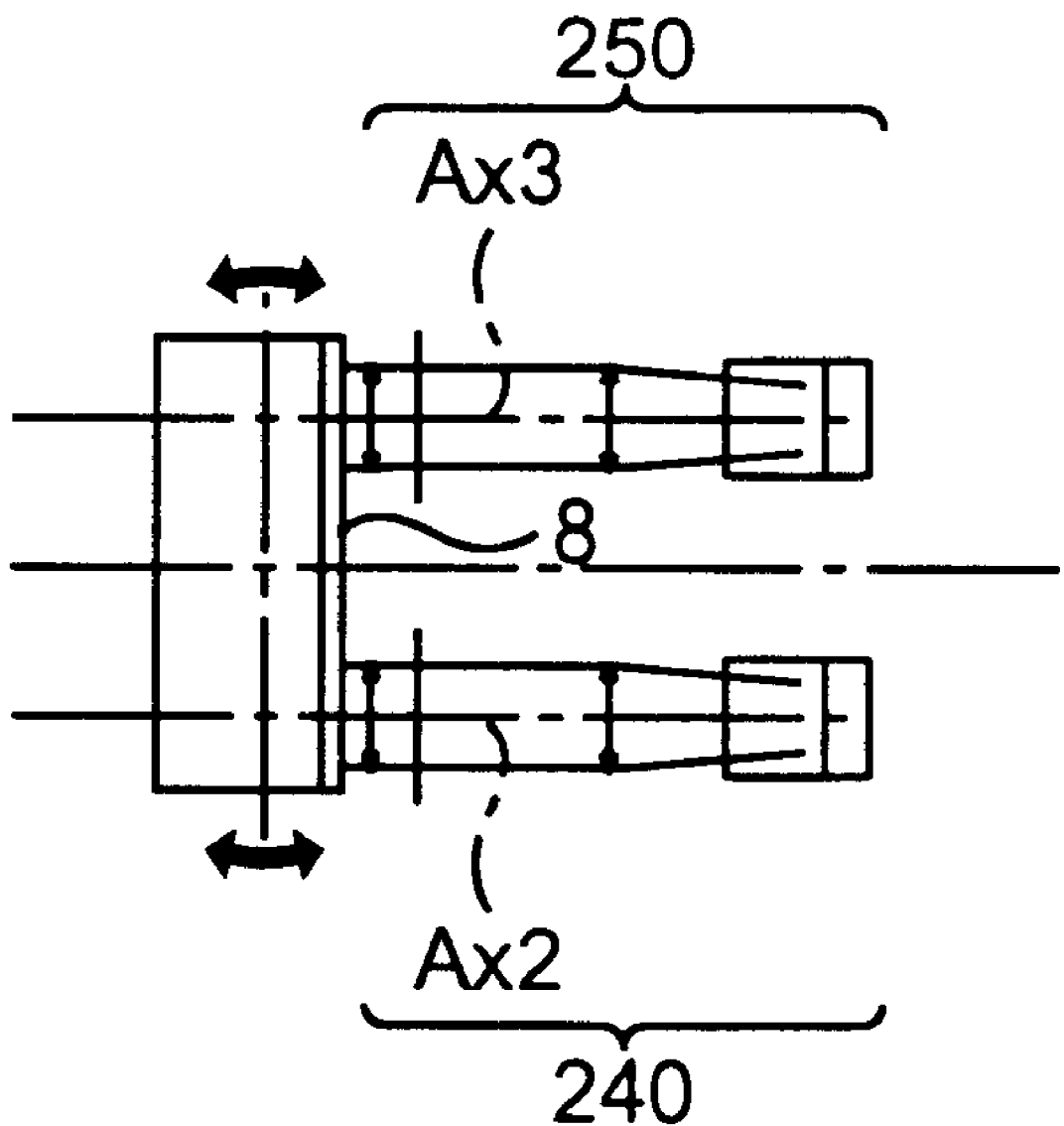
FIG. 32 is a plane view showing the overall construction of the microscope optical system in the eleventh embodiment.

The stereoscopic microscope 101 according to a eleventh embodiment of the present invention differs from the stereoscopic microscope 101 according to the tenth embodiment described above in that the bending direction by the reflecting mirror 8 is different 180 degree from that in the tenth embodiment. FIG. 31 is a side view of the microscope optical system 200 in the stereoscopic microscope 101 according to the tenth embodiment. FIG. 32 is a plan view of the same. Since the other configuration and function of the tenth embodiment are identical to those of the foregoing first embodiment, description thereof will be omitted here.

Incidentally, in the tenth embodiment, the reflecting mirror 8 may be replaced with a triangular prism in which incident light is internally reflected by its oblique face to be emitted therefrom.

Twelfth Embodiment

Figure 33:
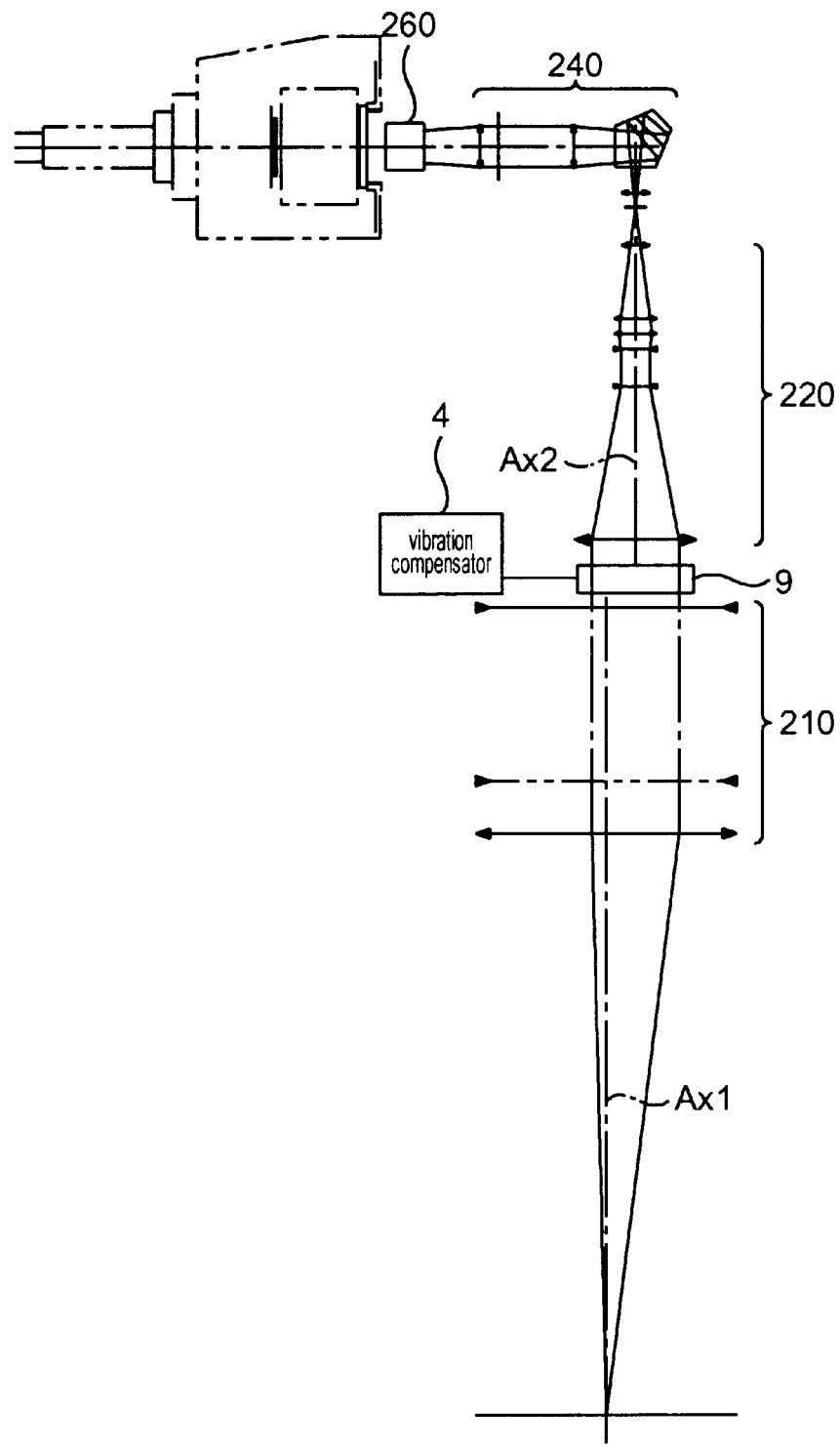
FIG. 33 is a side view showing an overall construction of the microscope optical system in twelfth embodiment of the present invention.
Figure 34:
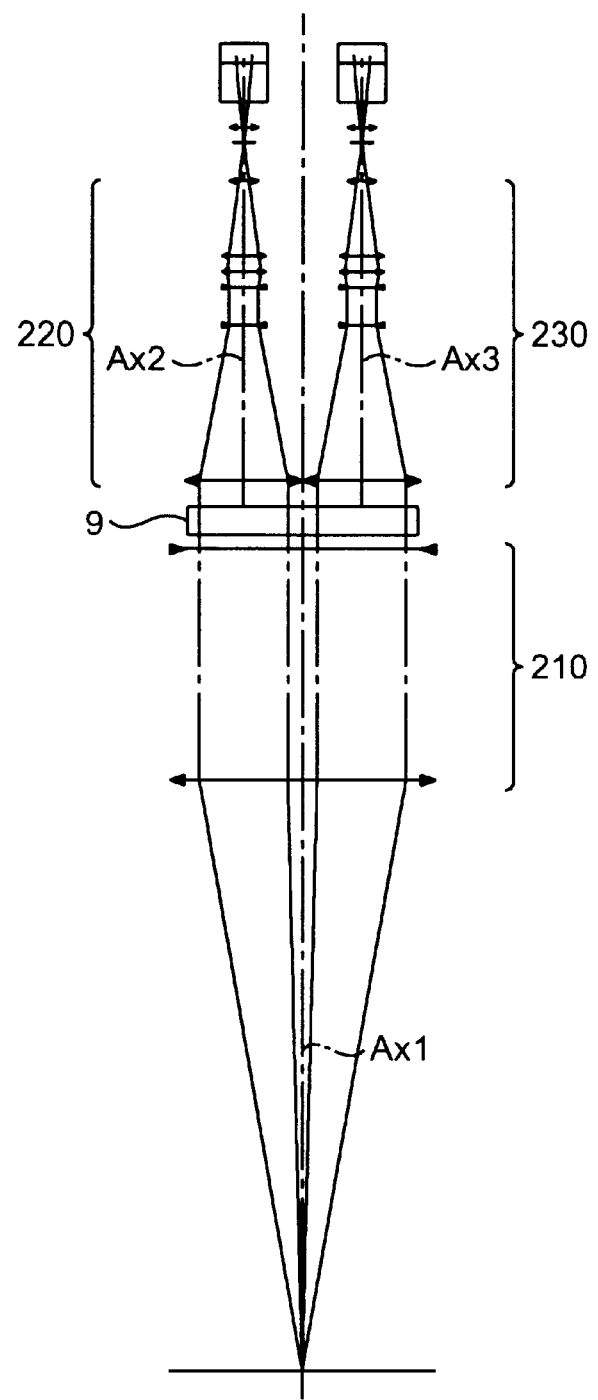
FIG. 34 is a front view showing the overall construction of the microscope optical system in the twelfth embodiment.

Twelfth through fifteenth embodiments of the present invention show examples where the microscope optical system 200 includes a variable-angle prism whose apical angle between both planar faces through which light passes are directed to an arbitrary direction and at an arbitrary angle to deflect the optical path. The twelfth embodiment is an example where a single variable-angle prism 9 for deflecting light incident on both the zoom optical systems 220, 230 is inserted between the close-up optical system 210 and the zoom optical systems 220, 230. FIG. 33 is a side view of the microscope optical system 200 in the stereoscopic microscope 101 according to the twelfth embodiment. FIG. 34 is a front view of the same. The variable-angle prism 9 applied in the twelfth embodiment has a structure that two transparent glass plates are sealed with bellows or the like, and liquid having a high refractive index is filled into the sealed space. In the present embodiment, the vibration compensator 4 has actuators for inclining one of the glass plates of the variable-angle prism 9 with respect to the other in two apical-angle variable directions, respectively, which are set to be orthogonal to each other on the surface of the other glass plate. Then, the vibration compensator 4 inclines the one glass plate with respect to the other glass plate in the apical-angle variable directions with the actuators, respectively. Thereby, the vibration compensator 4 can arbitrarily adjust the overall direction and the apical angle of the variable-angle prism 9. The vibration compensator 4 adjusts the variable-angle prism 9 in accordance with the control made by the microscope control unit 3, so that a principal ray originating from an object which existed at the center of the field at the point in starting time of the control is deflected to a direction parallel to the optical axes Ax2 and Ax3 of the individual zoom optical systems 220 and 230. Thereby, the image of the field formed on the image taking surface of the CCD 116 is fixed as long as the microscope control unit 3 keeps on controlling the vibration compensator 4. In the present embodiment, the use of the variable-angle prism 9 eliminates the need to bend the original optical path of the microscope optical system 200, in contrast to the foregoing embodiments using a reflecting mirror. Moreover, according to the present embodiment, only a single piece of variable-angle prism 9 is sufficient. Therefore, the vibration compensator 4 may have a relatively simple structure. Such a configuration allows a wider range of adjustment of the apical angle in the variable-angle prism 9. Since the other configuration and function of the twelfth embodiment are identical to those of the foregoing first embodiment, description thereof will be omitted here.

Figure 35:
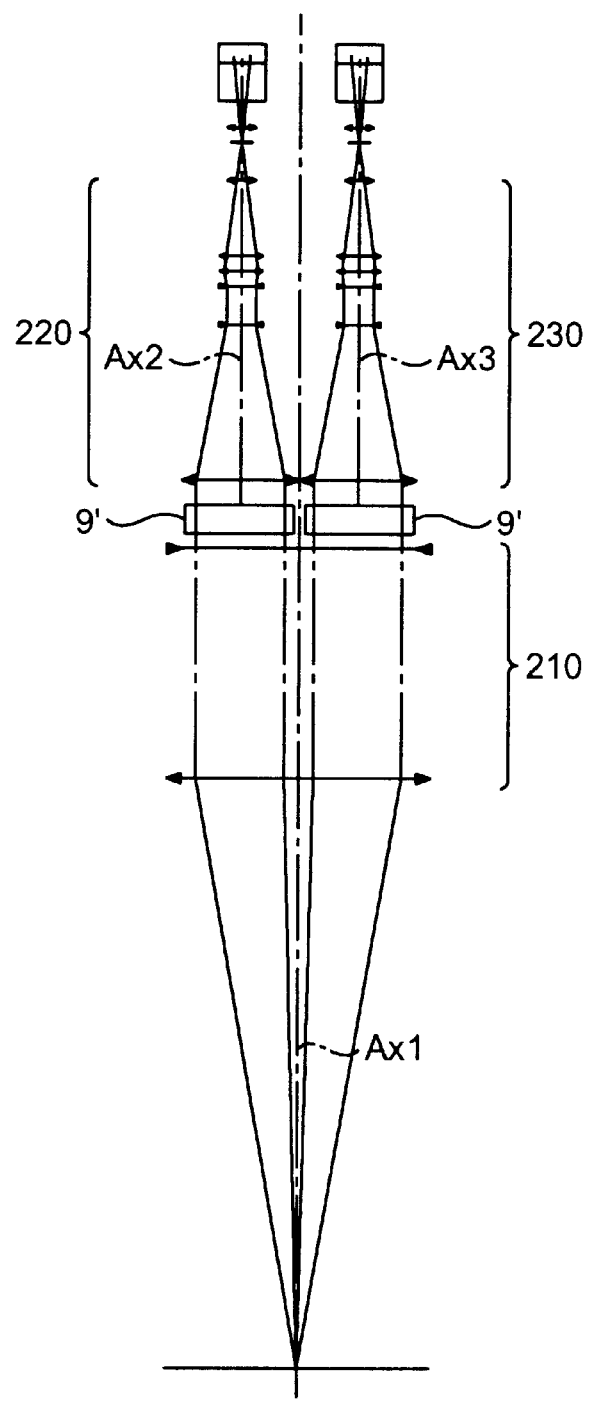
FIG. 35 is a front view showing variation of the twelfth embodiment.

Incidentally, in the twelfth embodiment, a pair of variable-angle prisms 9', 9' corresponding to the individual zoom optical systems 220, 230 may be inserted between the zoom optical systems 220, 230 and the close-up optical system 210, respectively, as shown in FIG. 35.

Thirteenth Embodiment

Figure 36:
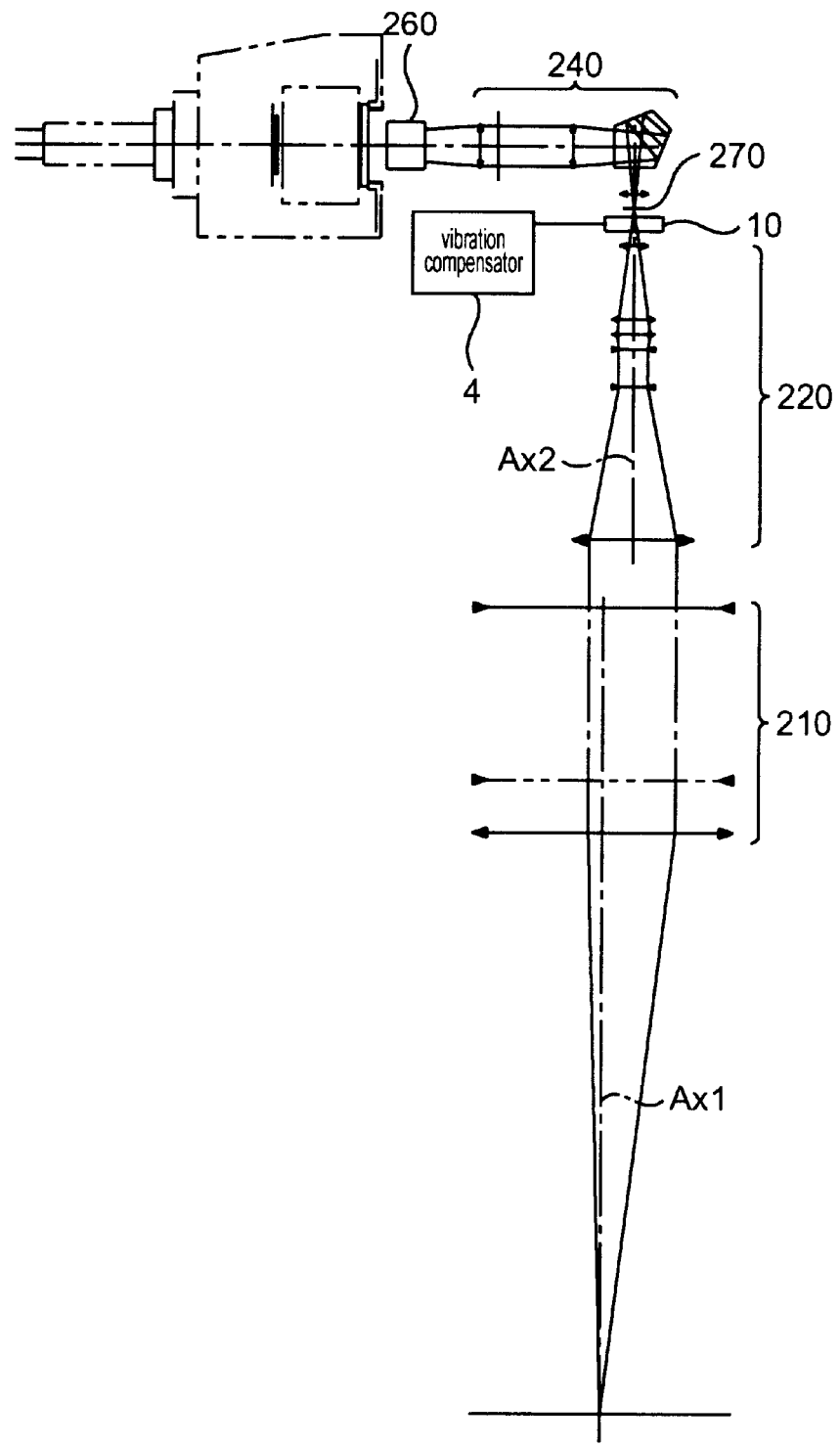
FIG. 36 is a side view showing an overall construction of the microscope optical system in thirteenth embodiment of the present invention.
Figure 37:
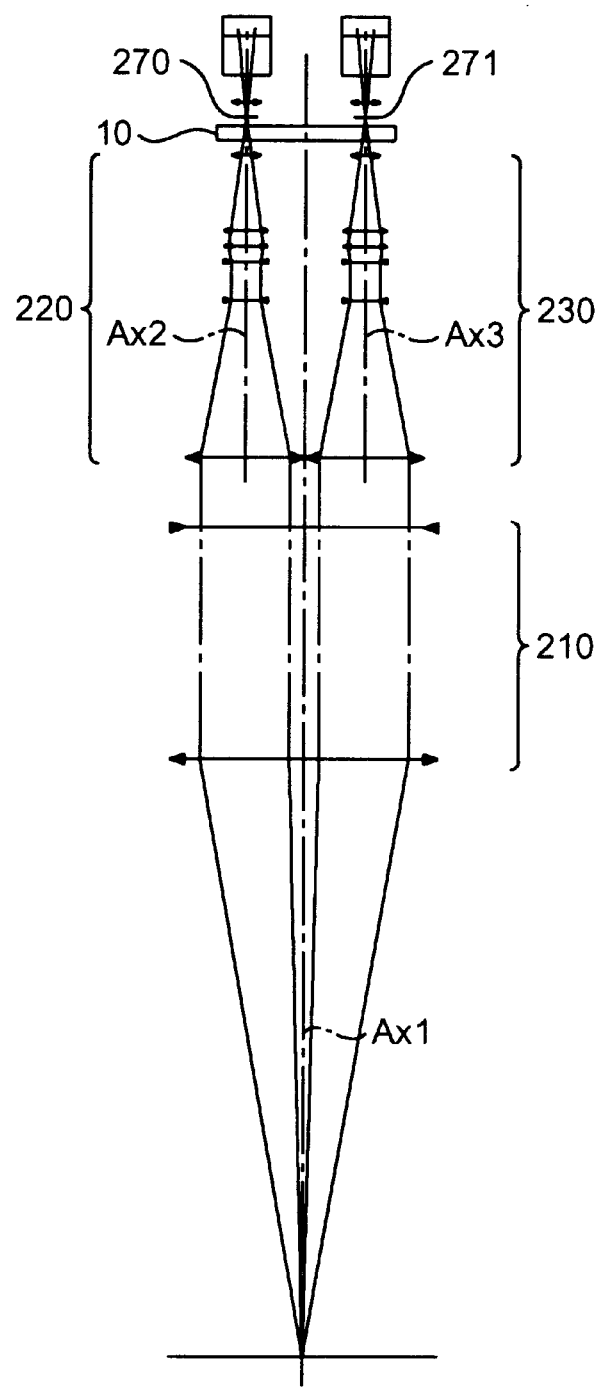
FIG. 37 is a front view showing the overall construction of the microscope optical system in the thirteenth embodiment.

The thirteenth embodiment is an example where a single variable-angle prism 10 is inserted between the both zoom optical systems 220, 230 and the both field stops 270, 271. FIG. 36 is a side view of the microscope optical system 200 in the stereoscopic microscope 101 according to the thirteenth embodiment. FIG. 37 is a plan view of the same. The variable-angle prism 10 and the vibration compensator 4 has the same structure as the twelfth embodiment described above to deflect light beams having passed through the individual zoom optical systems 220, 230 in arbitrary direction at arbitrary angle. The vibration compensator 4 adjust the variable-angle prism 10 in accordance with the control made by the microscope control unit 3, so that a principal ray originating from an object which existed at the center of the field at the point in starting time of the control is deflected to a direction parallel to the optical axes Ax2 and Ax3 of the relay optical systems 240 and 250. Thereby, the image of the field formed on the image taking surface of the CCD 116 is fixed as long as the microscope control unit 3 keeps on controlling the vibration compensator 4. Since the other configuration and function of the thirteenth embodiment are identical to those of the foregoing first embodiment, description thereof will be omitted here.

Figure 38:
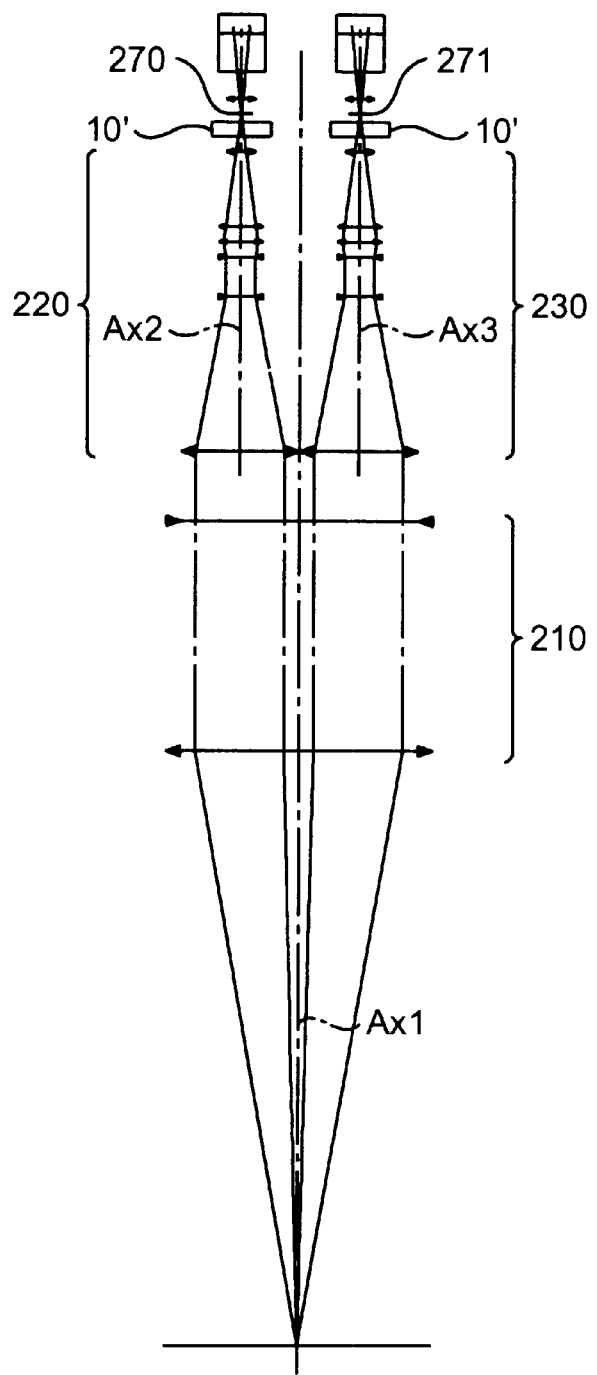
FIG. 38 is a front view showing variation of the thirteenth embodiment.

Incidentally, in the thirteenth embodiment, a pair of variable-angle prisms 10', 10' corresponding to the individual zoom optical systems 220, 230 may be inserted between the zoom optical systems 220, 230 and the field stops 270, 271, respectively, as shown in FIG. 38.

Fourteenth Embodiment

Figure 39:
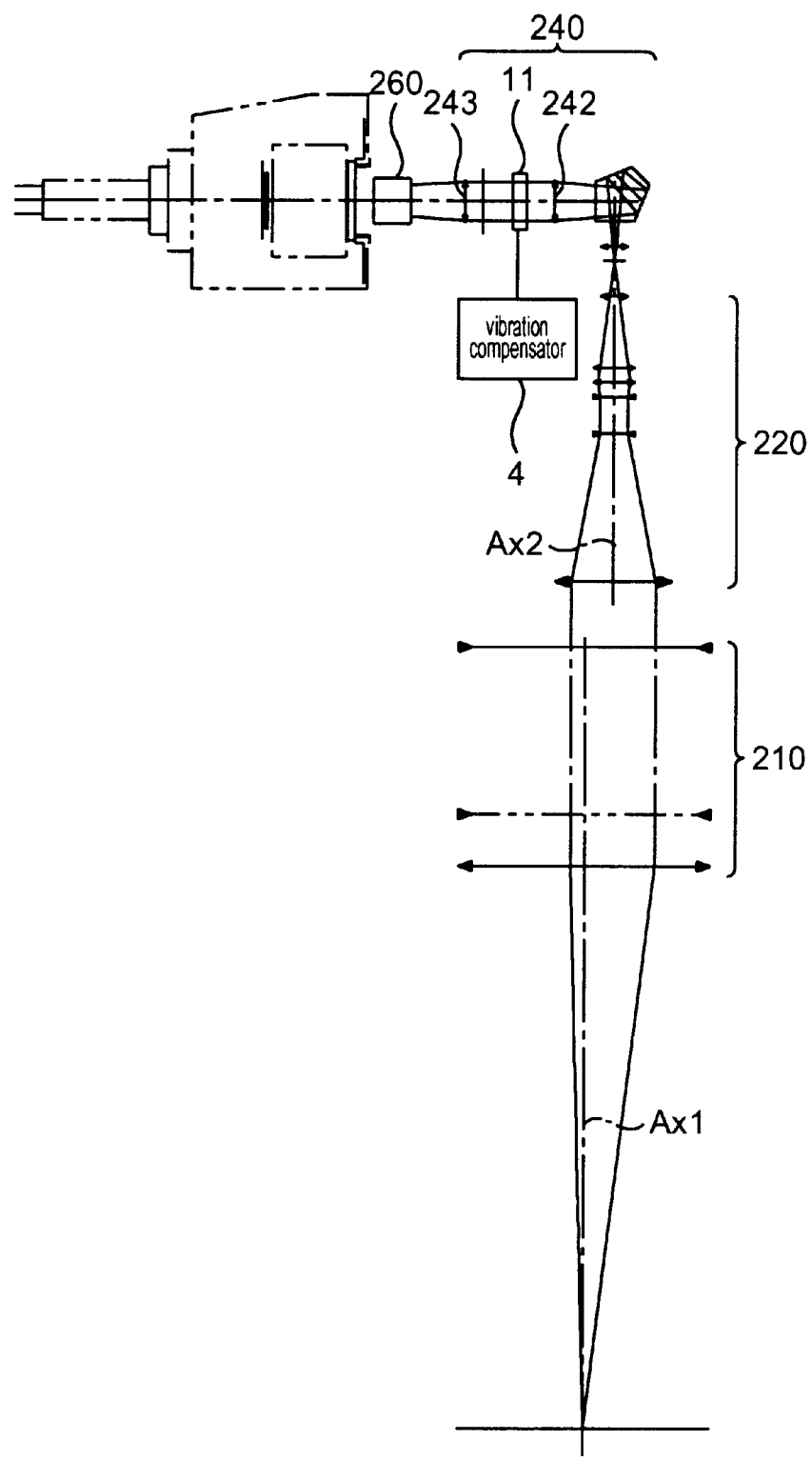
FIG. 39 is a side view showing an overall construction of the microscope optical system in fourteenth embodiment of the present invention.
Figure 40:
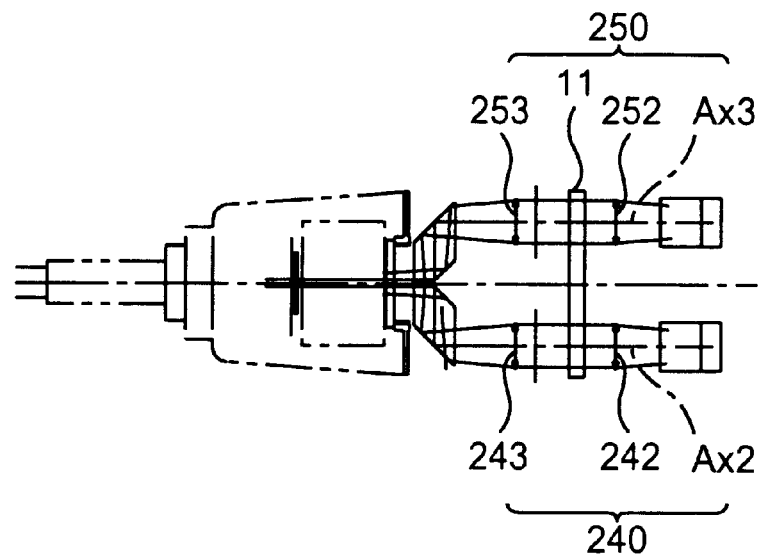
FIG. 40 is a plane view showing the overall construction of the microscope optical system in the fourteenth embodiment.

The fourteenth embodiment is an example where a single variable-angle prism 11 is inserted between the second lens groups 242, 252 and the third lens groups 243, 253 of the both relay optical systems 240, 250. FIG. 39 is a side view of the microscope optical system 200 in the stereoscopic microscope 101 according to the fourteenth embodiment. FIG. 40 is a plan view of the same. The variable-angle prism 11 and the vibration compensator 4 has the same structure as the twelfth embodiment described above to deflect light beams having passed through the individual second lens groups 242, 252 in arbitrary direction at arbitrary angle. The vibration compensator 4 adjust the variable-angle prism 11 in accordance with the control made by the microscope control unit 3, so that a principal ray originating from an object which existed at the center of the field at the point in starting time of the control is deflected to a direction parallel to the optical axes Ax2 and Ax3 of the relay optical systems 240 and 250. Thereby, the image of the field formed on the image taking surface of the CCD 116 is fixed as long as the microscope control unit 3 keeps on controlling the vibration compensator 4. Since the other configuration and function of the fourteenth embodiment are identical to those of the foregoing first embodiment, description thereof will be omitted here.

Figure 41:
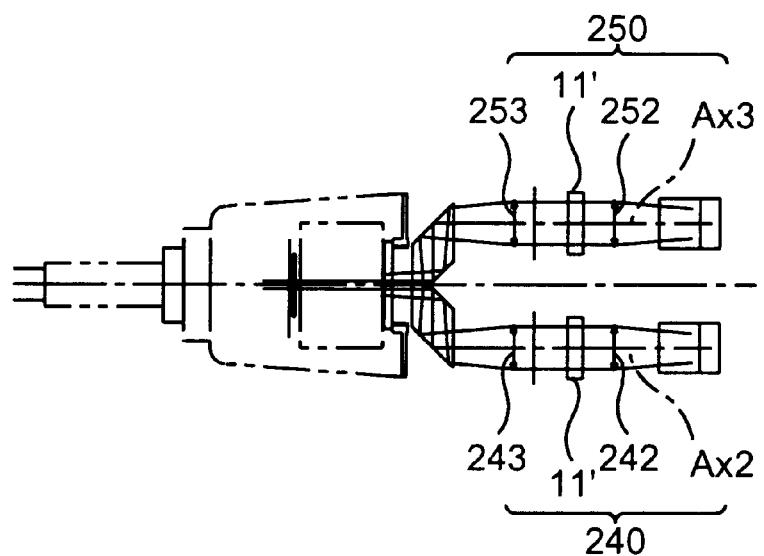
FIG. 41 is a plane view showing variation of the fourteenth embodiment.

Incidentally, in the fourteenth embodiment, a pair of variable-angle prisms 11', 11' corresponding to the individual relay optical systems 240, 250 may be inserted between the second lens groups 242, 252 and the third lens groups 243, 253 of the both relay optical systems 240, 250, respectively, as shown in FIG. 41. With this configuration, adjustable range of the apical angle of each variable-angle prism 11' can be expanded.

Fifteenth Embodiment

Figure 42:
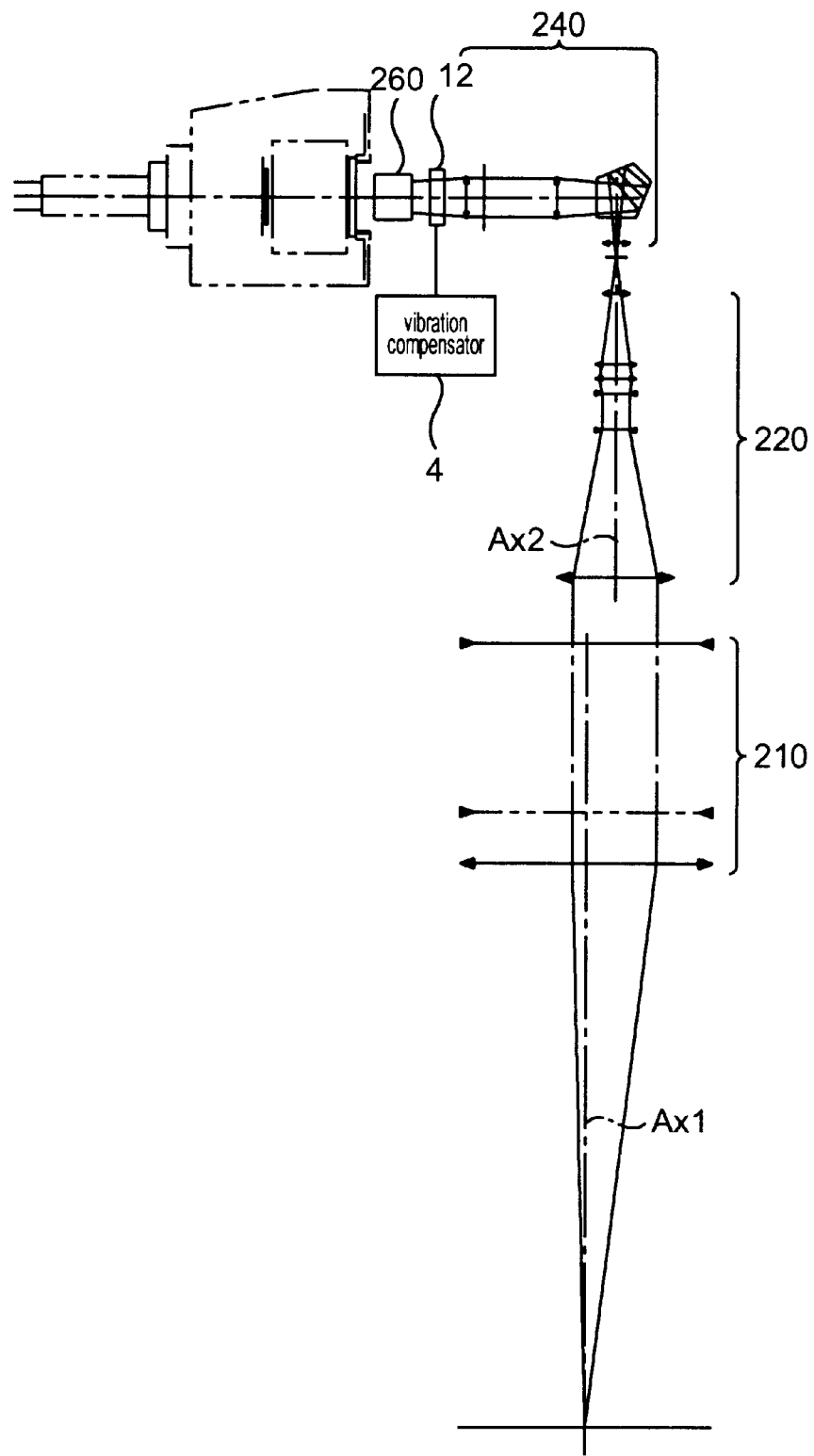
FIG. 42 is a side view showing an overall construction of the microscope optical system in fifteenth embodiment of the present invention.
Figure 43:
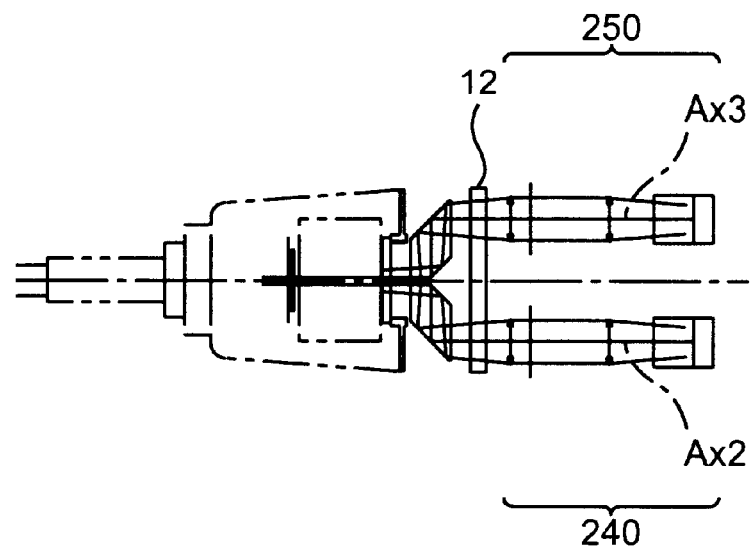
FIG. 43 is a plane view showing the overall construction of the microscope optical system in the fifteenth embodiment.

The fifteenth embodiment is an example where a single variable-angle prism 12 is inserted between the individual relay optical systems 240, 250 and the inter-axis distance reducing prism 260. FIG. 42 is a side view of the microscope optical system 200 in the stereoscopic microscope 101 according to the fifteenth embodiment. FIG. 43 is a plan view of the same. The variable-angle prism 12 and the vibration compensator 4 has the same structure as the twelfth embodiment described above to deflect light beams having passed through the relay optical systems 240, 250 in arbitrary direction at arbitrary angle. The vibration compensator 4 adjust the variable-angle prism 12 in accordance with the control made by the microscope control unit 3, so that a principal ray originating from an object which existed at the center of the field at the point in starting time of the control is deflected to a direction parallel to the optical axes Ax2 and Ax3 of the relay optical systems 240 and 250. Thereby, the image of the field formed on the image taking surface of the CCD 116 is fixed as long as the microscope control unit 3 keeps on controlling the vibration compensator 4. Since the other configuration and function of the fifteenth embodiment are identical to those of the foregoing first embodiment, description thereof will be omitted here.

Figure 44:
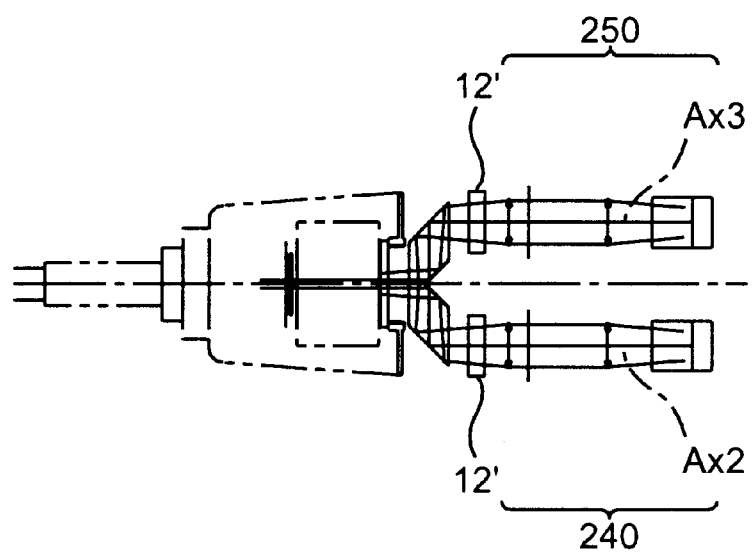
FIG. 44 is a plane view showing variation of the fifteenth embodiment.

Incidentally, in the fifteenth embodiment, a pair of variable-angle prisms 12', 12' corresponding to the individual relay optical systems 240, 250 may be inserted between the individual relay optical systems 240, 250 and the inter-axis distance reducing prism 260, respectively, as shown in FIG. 44. With this configuration, adjustable range of the apical angle of each variable-angle prism 12' can be expanded.

Sixteenth Embodiment

Figure 45:
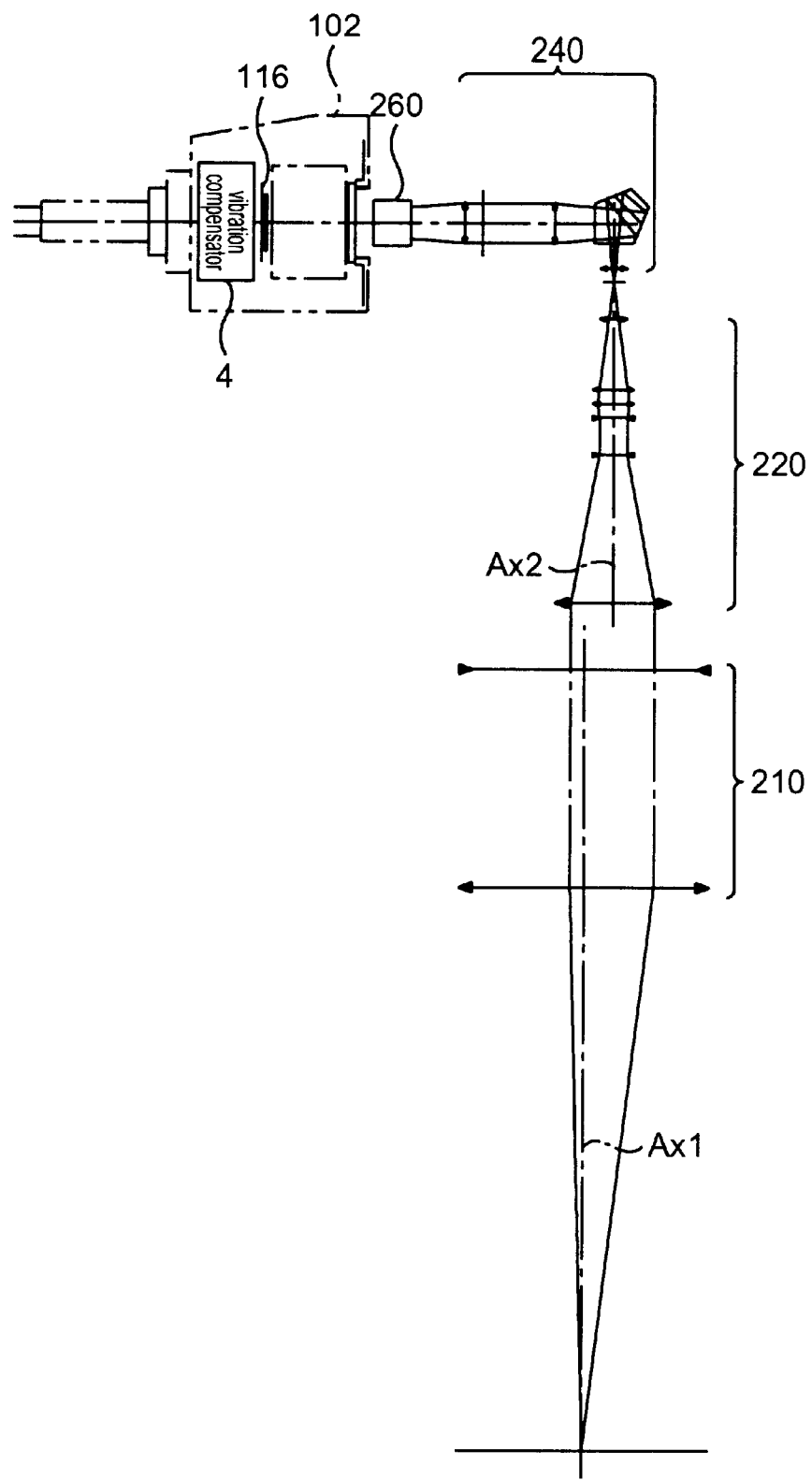
FIG. 45 is a side view showing an overall construction of the microscope optical system in sixteenth embodiment of the present invention.
Figure 46:
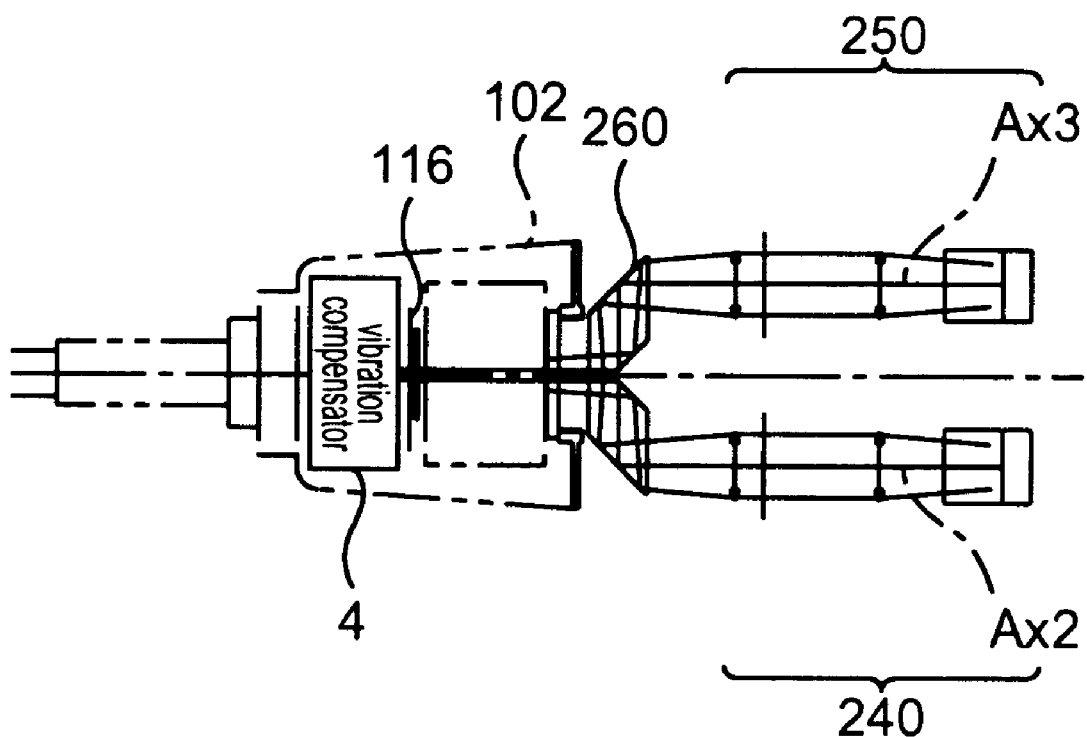
FIG. 46 is a plane view showing the overall construction of the microscope optical system in the sixteenth embodiment.

A sixteenth embodiment of the present invention shows an example where the image pickup device, or the CCD 116, is moved inside the HDTV-CCD camera 102 within a plane including its image taking surface. FIG. 45 is a side view of the microscope optical system 200 in the stereoscopic microscope 101 according to the sixteenth embodiment. FIG. 46 is a plan view of the same.

In the sixteenth embodiment, the CCD 116 is held in the HDTV-CCD camera 102 so as to be movable within the plane including its image taking surface. The vibration compensator 4 has two pairs of actuators for moving this CCD 116 in two orthogonal directions, respectively, within the plane including the image taking surface. Then, the vibration compensator 4 moves the CCD 116 to an arbitrary position with the individual actuators in accordance with the control made by the microscope control unit 3, so that object light originating from the field at the point of starting control is incident on a fixed position on the image taking surface of the CCD 116. Thereby, the image of the field formed on the image taking surface of the CCD 116 is fixed as long as the microscope control unit 3 keeps on controlling the vibration compensator 4.

As has been described, according to the antivibration microscope of the present invention, image blur can be prevented even in a microscope that has a high probability of producing image blur as great as recognizable to observer's eyes in case it is held at the extremity of an arm of a pedestal for use.

I claim:

1. An antivibration microscope comprising:
    a microscope optical system which forms an image of an object lying in a field of a predetermined size, working distance L of said microscope optical system satisfing the condition $1/A_V > 1/(11.46+0.011 \times L)$, where $A_V$ is the width of said field;

a first sensor for measuring inclination of the whole microscope optical system;

a second sensor for measuring movement of the whole microscope optical system;

a deflecting device which deflects object light traveling through said microscope optical system to an arbitrary direction at an arbitrary angle; and a controlling unit for adjusting the direction and angle of deflection for said object light by said deflecting device based on the measurements by said first sensor and said second sensor, whereby said image is steady in spite of the inclination or the movement of the microscope optical system.

2. The antivibration microscope according to claim 1, wherein
    said microscope optical system shoots a real image of the object lying in said field, to be displayed on a monitor.

3. The antivibration microscope according to claim 1, wherein:
    said microscope optical system includes a plurality of lenses each having a power; and
    said deflecting device shifts only a part of the lenses included in said microscope optical system, within a plane orthogonal to its optical axis.

4. The antivibration microscope according to claim 1, wherein:
    said microscope optical system includes a reflecting mirror for bending its optical axis; and
    said deflecting device inclines said reflecting mirror to an arbitrary direction at an arbitrary angle.

5. The antivibration microscope according to claim 1, wherein
    said deflecting device includes a variable-angle prism inserted into said microscope optical system.

6. An antivibration microscope comprising:
    a microscope optical system which forms an image of an object lying in a field of a predetermined size, working distance L of said microscope optical system satisfiing the condition $1/A_V > 1/(11.46+0.011 \times L)$, where $A_V$ is the width of said field;

an image pickup device having an image taking surface which picks up the image formed on the image taking surface by said microscope optical system;

a first sensor for measuring inclination of the whole microscope optical system;

a second sensor for measuring movement of the whole microscope optical system; and a controlling unit for moving said image pickup device within a plane including the image taking surface based on the measurements by said first sensor and said second sensor so that the image of the object, lying in a predetermined field, formed by said microscope optical system can be picked up at a fixed position on the image taking surface of said image pickup device.

* * * * *